(12) United States Patent
Arnold et al.

(10) Patent No.: US 11,202,684 B2
(45) Date of Patent: Dec. 21, 2021

(54) AUTOMATED INSERTION DEVICE

(71) Applicant: XACT ROBOTICS LTD., Caesarea (IL)

(72) Inventors: Ofer Arnold, Ma'ale Tzvia (IL); Eduard Borodets, Nazereth Illit (IL)

(73) Assignee: XACT ROBOTICS LTD., Caesarea (IL)

( * ) Notice: Subject to any disclaimer, the term of this patent is extended or adjusted under 35 U.S.C. 154(b) by 457 days.

(21) Appl. No.: 16/303,536

(22) PCT Filed: May 25, 2017

(86) PCT No.: PCT/IL2017/050584
§ 371 (c)(1),
(2) Date: Nov. 20, 2018

(87) PCT Pub. No.: WO2017/203531
PCT Pub. Date: Nov. 30, 2017

(65) Prior Publication Data
US 2019/0290372 A1   Sep. 26, 2019

Related U.S. Application Data

(60) Provisional application No. 62/341,097, filed on May 25, 2016.

(51) Int. Cl.
*A61B 34/32* (2016.01)
*A61B 34/00* (2016.01)
(Continued)

(52) U.S. Cl.
CPC .............. *A61B 34/32* (2016.02); *A61B 34/00* (2016.02); *A61M 5/31501* (2013.01);
(Continued)

(58) Field of Classification Search
CPC ......... A61B 34/32; A61B 34/00; A61B 34/30; A61B 2034/301; A61B 2090/064;
(Continued)

(56) References Cited

U.S. PATENT DOCUMENTS

| 7,008,373 B2 | 3/2006 | Stoianovici et al. |
| 8,348,861 B2 | 1/2013 | Glozman et al. |

(Continued)

FOREIGN PATENT DOCUMENTS

| CN | 101972159 A | 2/2011 |
| CN | 102069496 | 5/2011 |

(Continued)

OTHER PUBLICATIONS

PCT Search Report for International Application No. PCT/IL2017/050584; dated Aug. 27, 2017; 3 pp.

(Continued)

*Primary Examiner* — Anh T Dang
(74) *Attorney, Agent, or Firm* — The Roy Gross Law Firm, LLC; Roy Gross

(57) ABSTRACT

A device for insertion of a medical tool held in an end effector, the device comprising moveable platforms providing motion in two generally orthogonal directions, and two piston mechanisms operating within cylinders, coupled to the moveable platforms, and being attached at their distal end to the end effector by means of a common joint. The pistons may be linear actuators. The end effector is manipulated by driving mechanisms propelling the pistons linearly. The proximal ends of the cylinders may be coupled to a common shaft. The axes of the cylinders and the pistons, the line connecting the pistons axes through the common joint and the axis of the cylinders' common shaft may all be located substantially in a single plane. Coordinated motion of the moveable platforms and the piston mechanisms (Continued)

enables the maintenance of a virtual remote center of motion of the medical tool as its orientation changes.

20 Claims, 15 Drawing Sheets

(51) Int. Cl.
*A61M 5/46* (2006.01)
*A61M 5/315* (2006.01)
*A61B 34/30* (2016.01)
*A61B 90/00* (2016.01)
*A61B 90/11* (2016.01)
*A61B 17/34* (2006.01)

(52) U.S. Cl.
CPC .............. *A61M 5/46* (2013.01); *A61B 34/30* (2016.02); *A61B 90/11* (2016.02); *A61B 2017/3409* (2013.01); *A61B 2034/301* (2016.02); *A61B 2090/064* (2016.02)

(58) Field of Classification Search
CPC .. A61B 90/11; A61B 2017/3409; A61M 5/46; A61M 5/3151
See application file for complete search history.

(56) References Cited

U.S. PATENT DOCUMENTS

| | | | |
|---|---|---|---|
| 8,663,130 B2 | 3/2014 | Neubach et al. | |
| 2006/0229641 A1 | 10/2006 | Gupta et al. | |
| 2009/0112119 A1 | 4/2009 | Kim | |
| 2012/0182134 A1* | 7/2012 | Doyle | A61B 34/30 340/12.22 |
| 2014/0371584 A1 | 12/2014 | Cleary et al. | |
| 2014/0378899 A1 | 12/2014 | Hoffmann et al. | |
| 2016/0249990 A1 | 9/2016 | Glozman et al. | |
| 2016/0249991 A1 | 9/2016 | Glozman et al. | |
| 2016/0317240 A1 | 11/2016 | Vogele | |

FOREIGN PATENT DOCUMENTS

| | | |
|---|---|---|
| CN | 104323861 | 4/2015 |
| CN | 104739512 A | 7/2015 |
| WO | 2016084092 | 6/2016 |
| WO | 2017042823 | 3/2017 |
| WO | 2017115370 | 7/2017 |
| WO | 2017179044 | 10/2017 |

OTHER PUBLICATIONS

PCT Written Opinion for International Application No. PCT/IL2017/050584; dated Aug. 27, 2017 ; 5 pp.

PCT Preliminary Report for International Application No. PCT/IL2017/050584; dated ; Nov. 27, 2018; 6 pp.

* cited by examiner

AUTOMATED INSERTION DEVICE

RELATED APPLICATIONS

This application is a National Phase of PCT Patent Application No. PCT/IL2017/050584 having International filing date of May 25, 2017, which claims the benefit of priority of U.S. Provisional Application No. 62/341,097 filed on May 25, 2016. The contents of the above applications are all incorporated by reference as if fully set forth herein in their entirety.

FIELD OF THE INVENTION

The present invention relates to the field of interventional procedures, and specifically to devices, systems and methods for automated insertion of a medical tool into a target within the body of a subject.

BACKGROUND

Many routine treatments employed in modern clinical practice involve percutaneous insertion of medical tools, such as needles and catheters, for biopsy, drug delivery and other diagnostic and therapeutic procedures. The aim of an insertion procedure is to place the tip of an appropriate medical tool safely and accurately in a target region, which could be a lesion, tumor, organ or vessel. Examples of treatments requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation and various minimally invasive surgeries.

Guidance and steering of needles in soft tissue is a complicated task that requires good three-dimensional coordination, knowledge of the patient's anatomy and a high level of experience. Therefore, image-guided automated (e.g., robotic) systems have been proposed for performing these functions. Among such systems are those described in U.S. Pat. No. 7,008,373 to Stoianovici, for "System and method for robot targeting under fluoroscopy", U.S. Pat. No. 8,348,861 to Glozman et al, for "Controlled Steering of a Flexible Needle", U.S. Pat. No. 8,663,130 to Neubach et al, for "Ultrasound Guided Robot for Flexible Needle Steering" and U.S. patent application Ser. No. 15/027,439 to Glozman et al, for "Gripper for Robotic Image Guided Needle Insertion".

In recent years, body mounted automated devices have been introduced. Some of these devices are guiding devices that help in choosing the insertion point and in aligning the needle with the insertion point and with the target, and the physician then inserts the needle manually. Others are steering devices that also insert the needle towards the target, as disclosed, for example, in U.S. Application Publication No. 2006/0229641 to Gupta et al, for "Guidance and Insertion System", U.S Application Publication No. 2009/0112119 to Kim, for "Rotating Biopsy Device and Biopsy Robot", U.S. Application Publication No. 2014/0371584 to Cleary et al, for "Patient Mounted MRI and CT Compatible Robot for Needle Guidance in Interventional Procedures", and U.S. Patent Application Publication No. 2016/0249990 to Glozman et al, for "Needle Steering by Shaft Manipulation".

However, there is still a need for an automated insertion device which is capable of steering a medical tool into a target within the patient's body accurately and reliably, and which provides a large angular workspace for the medical tool while maintaining a low-profile workspace for the insertion device.

The disclosures of each of the publications mentioned in this section and in other sections of the specification, are hereby incorporated by reference, each in its entirety.

SUMMARY

The present disclosure describes new exemplary automated systems and devices for insertion of medical tools (e.g. needles) into a subject's body for diagnostic and/or therapeutic purposes.

In some implementations, an insertion system is disclosed, which includes an insertion device, a processor and a controller. The insertion system may be configured to operate in conjunction with an imaging system. The utilized imaging modality may be any one of X-ray fluoroscopy, CT, cone beam CT, CT fluoroscopy, MRI, ultrasound, or any other suitable imaging modality.

The processor may be configured, inter alia, to receive, process and show on a display images from an imaging system (e.g., CT, MRI), to calculate the optimal pathway for the medical tool (e.g., needle) from an entry point to the target while avoiding obstacles en route, and to provide instructions to steer the needle toward the target according to the calculated optimal pathway. In some implementations, needle steering is controlled in a closed-loop manner, i.e., the processor generates motion commands to the insertion device via the controller and receives feedback regarding the actual location of the needle, which is then used for real-time pathway corrections. The optimal pathway, as well as pathway corrections, may be calculated and executed either on a two-dimensional plane or in the three-dimensional space. In some implementations, the entry point, the target and the obstacles, such as bones or blood vessels, are manually marked by the physician on one or more of the obtained images.

Automatic needle insertion and real-time steering has many advantages over manual needle insertion. For example, it obviates the need to withdraw and re-insert the needle, as is often required when the physician manually inserts the needle and fails to reach the target, for example, due to tissue movement as the needle is being inserted into the body. Also, automatic needle steering improves the accuracy of the procedure, which enables reaching small targets, thus allowing earlier detection of malignant neoplasms, for example. In addition, it provides increased safety for the patient, as there is a significant lower risk of human error. Further, such a procedure is safer for the medical personnel, as it minimizes their radiation exposure during the procedure. Since the automated device can be controlled from a remote site, even from outside of the hospital, there is no longer a need for the physician to be present in the procedure room.

In some implementations, the insertion device comprises at least one moveable platform, two piston mechanisms coupled to the at least one moveable platform, and an end effector, to which the medical tool is coupled, either directly or by means of an insertion module. Each piston mechanism may include a cylinder, a piston positioned, at least in part, within the cylinder, and a driving mechanism configured to propel the piston in and out of the cylinder in order to manipulate the end effector. In some implementations, the distal ends of the two pistons may be coupled to a common joint, and the proximal ends of the cylinders may be coupled either to a common shaft or each to a separate shaft. In some implementations, the cylinders, pistons, the pistons' common joint and the cylinders' shaft/s are all located substantially in a single plane, allowing larger angular movement and thus a larger workspace for the insertion device's end effector and medical tool. It can be appreciated that the cylinders, pistons, pistons' common joint and cylinders' shaft/s being located substantially in a single plane, may specifically refer to the axes (i.e., longitudinal axes) of the cylinders, pistons and cylinder shaft/s, and the line connecting between the pistons' axes through the common joint, all being located in a single plane. In some implementations, the axis of the cylinders' common shaft (or the axes of the separate shafts) may be parallel to the line connecting between the pistons' axes through the common joint, such that the axis (or axes) of the cylinder shaft (or shafts), the line connecting between the pistons' axes through the common joint, and the axes of the cylinders and of the pistons, may essentially form a trapeze shape.

The piston and cylinder mechanisms are described and illustrated throughout this disclosure as motor driven linear actuator assemblies, with the activated rod being called the "piston", and the thrust tube or outer housing being termed the "cylinder", by analogy with a fluid operated device. However, it is to be understood that although electric motor actuated devices are generally understood to be the simplest and most controllable implementations, it is possible to implement the devices also using conventional pneumatic or hydraulic cylinders with their associated pistons. Therefore, the terms cylinders and pistons when used throughout this disclosure, and when claimed, are understood to include any controllable linear motion-generating devices.

In some implementations, the end effector may be coupled to one of the at least one moveable platforms of the insertion device via one or more gimbals. For example, the end effector may be coupled to the moveable platform by means of two gimbals; the first gimbal being located at its top end and the second gimbal being located at its bottom end. In some implementations, the first (top) gimbal may be coupled to the pistons' common joint via an axial joint, and the second (bottom) gimbal may be coupled to an extending arm member of the moveable platform via another axial joint, such that propulsion of the pistons in and out of the cylinders results in rotation of the gimbal/s while the cylinders, the pistons, the pistons' common joint and the cylinder shaft/s all remain in a single plane.

The combination of the extending arm and piston mechanisms distances the end effector, and thus the needle coupled to the end effector, from the metallic components of the insertion device (e.g., motors and gears), and thus minimizes imaging artifacts in the area proximate the needle, which is scanned, in image-guided procedures, to follow and determine the position of the needle during the insertion procedure.

In some implementations, the insertion device may have several degrees of freedom (DOF). For example, the device may have five DOFs: forward-backward and left-right linear translations, front-back and left-right rotations, and longitudinal needle translation toward the subject's body. In some implementations, the device may comprise a Z platform, an X platform and a top assembly, the top assembly including the two piston mechanisms. The Z platform and the X platform may each include a portion of a driving mechanism, such as a ball screw mechanism, which propels the X platform along the Z axis, on top of the Z platform. The X platform and the top assembly may each include a portion of another driving mechanism, which may also be a ball screw mechanism, which propels the top assembly along the X axis, which may be perpendicular to the Z axis, on top of the X platform. The combination of the Z platform, the X platform and the top assembly thus enables full planar movement of the top assembly, and thus of the end effector coupled thereto. In some implementations, each piston mechanism of the top assembly may include a cylinder and a piston which is moveable in and out of the cylinder, for example via a ball screw mechanism. Controlling the pistons' movements provides the device with two rotational DOFs. In some implementations, longitudinal needle translation is enabled by means of an insertion mechanism, which may be coupled to the end effector or divided between the end effector and an insertion module which is coupleable to the end effector and which includes the needle.

Although a linear needle trajectory is generally preferred, a linear trajectory may not always be possible to plan, due to the location of the target (e.g., tumor, lesion), the presence of obstacles (e.g., bones, blood vessels), etc., thus the planned trajectory may have a certain degree of curvature. Further, even if the planned trajectory is linear, it may not always be possible to follow the planned linear trajectory due to movements of the target and/or the obstacles during the insertion procedure, for example. In such cases, the needle trajectory may be adjusted during the insertion procedure, as described, for example, in abovementioned U.S. Pat. No. 8,348,861.

In some implementations, the Remote Center of Motion (RCM) of the end effector may be virtual and located at the needle entry point on the body of the subject, i.e., the virtual RCM is not fixed by design, but changes according to the chosen entry point. Once the needle entry point is selected, the user may set the selected entry point as the virtual RCM. The system's software can then determine, using a reverse kinematics algorithm, as described, for example, in abovementioned U.S. Pat. No. 8,348,861, the linear movements required from the X platform and/or the top assembly, while the end effector is being rotated, in order to maintain the entry point as the virtual RCM. The virtual RCM being located at the needle's entry point prevents skin/tissue tearing if a linear trajectory is not possible to follow and/or if the planned trajectory (linear or otherwise) requires adjustment as the needle is being inserted into the patient's body.

In some implementations, the overall angular workspace of the needle may form a cone shape, with its vertex being the virtual RCM, i.e., at the selected needle entry point.

There is thus provided in accordance with an exemplary implementation of the devices described in this disclosure, a an automated device for inserting a medical tool into a body of a subject, comprising:
 (i) at least one moveable platform,
 (ii) a first and a second piston mechanisms, each piston mechanism comprising:
  a cylinder,
  a piston, at least a portion of the piston being positioned within the cylinder, and
  a driving mechanism configured to controllably propel the piston in and out of the cylinder, and
 (iii) an insertion mechanism configured to impart movement to the medical tool in the direction of the body of the subject,
 wherein the distal ends of the pistons of the first and second piston mechanisms are coupled to a common joint.

In such an automated device, the axes of the cylinders and of the pistons, and a line connecting the points of coupling of the pistons with the common joint, may all be located substantially in a single plane. The axes may be the longitudinal axes of the cylinders and of the pistons.

Further, in such an automated device, the distal ends of the pistons of the first and second piston mechanisms may be coupled to the common joint via piston end joints, each piston end joint having at least one rotational degree of freedom. In either of the above two devices, the proximal ends of the cylinders of the first and second piston mechanisms may be coupled to a single shaft, also located in the single plane. In that case, the proximal ends of the cylinders may be coupled to the single shaft via cylinder end joints, each cylinder end joint having at least one rotational degree of freedom.

Additionally, in alternative implementations of any of the above-described, the at least one moveable platform may comprise:

(i) a first platform adapted to move in a first linear direction, and (ii) a second platform coupled to the first platform and adapted to move in a second linear direction substantially perpendicular to the first linear direction, wherein the first and second piston mechanisms are coupled to the second platform.

Furthermore, in any of these devices, the driving mechanism may comprise a threaded shaft and an internally threaded nut operatively coupled to the threaded shaft and rigidly connected to the piston, such that rotation of the threaded shaft results in linear movement of the piston.

Still other example implementations of the above described devices may further comprise an end effector coupled to the common joint. The end effector may be coupled to the common joint via a first gimbal, and the first gimbal may be coupled to the common joint via a rotational joint.

In any of the above described devices, the second platform may further comprise an extending arm and a second gimbal coupled to the extending arm. At least a first portion of the insertion mechanism may then be coupled to the end effector. In the latter case, the device may further comprise an insertion module, the insertion module comprising the medical tool and at least a second portion of the insertion mechanism, the first portion of the insertion mechanism being configured for operative coupling to the first portion of the insertion mechanism.

In any of the above described devices the automated device may comprise a virtual Remote Center of Motion located at a selected entry point on the body of the subject, and then, the angular workspace of the medical tool should form a cone shape, the vertex of the cone being located at the virtual Remote Center of Motion.

Further implementations involve devices as previously described, further comprising at least one registration element. The previously described devices may further comprise a base adapted for securing to the body of the subject. In the latter case, the base may comprise a printed circuit board, and the automated device may further comprise at least one electrical wire configured to connect the printed circuit board to at least one additional printed circuit board of the at least one moveable platform. The one or more of the at least one electrical wires may then comprise a flat flex cable.

Yet other implementations may involve an automated device according to any of the above mentioned implementations, further comprising one or more sensors configured to be coupled to one or more of the at least one moveable platform, the first piston mechanism and the second piston mechanism. In such a case, at least a first sensor of the one or more sensors may be configured to measure a parameter associated with the interaction between the medical tool and a bodily tissue. The first sensor may be a force sensor.

In any of the above described automated devices comprising sensors, at least a second sensor of the one or more sensors may be configured to monitor the movement of one or more of the at least one moveable platform, the first piston and the second piston.

There is further provided, according to additional implementations of this disclosure, an automated device for inserting a medical tool into a body of a subject, comprising:

(i) a device base, (ii) a first platform coupled to the device base and comprising a first portion of a first driving mechanism, (iii) a second platform coupled to the first platform and comprising:

a second portion of the first driving mechanism, the first driving mechanism being configured to propel the second platform in a first linear direction, and a first portion of a second driving mechanism, (iv) a third platform coupled to the second platform and comprising:

a second portion of a second driving mechanism, the second driving mechanism being configured to propel the third platform in a second linear direction substantially perpendicular to the first linear direction, and first and second pistons connected to a common joint at their distal ends, and (v) an end effector coupled to the common joint and configured for coupling the medical tool thereto.

In such automated devices, the axes of the first and second pistons and a line connecting the piston axes through the common joint, may be located substantially in a single plane.

Such an automated device may further comprise an insertion module comprising the medical tool and configured to be coupled to the end effector. Additionally, in such an automated device, the end effector may comprise a first portion of a third driving mechanism and the insertion module may comprise a second portion of the third driving mechanism operatively coupleable to the first portion of the third driving mechanism, and the third driving mechanism may be configured to impart movement to the medical tool in the direction of the body of the subject.

In alternative further implementations, the automated device may further comprise:

(vi) first and second cylinders, wherein at least a portion of the first piston is positioned within the first cylinder, and at least a portion of the second piston is positioned within the second cylinder, (vii) a fourth driving mechanism configured to controllably propel the first piston in and out of the first cylinder, and (viii) a fifth driving mechanism configured to controllably propel the second piston in and out of the second cylinder.

In such a configuration, the proximal ends of the first and second cylinders may be coupled to a single shaft, and the axes of the first and second cylinders and of the single shaft may be located in the single plane. Furthermore, in any of these automated devices, the end effector may be coupled to the common joint via a first gimbal, in which case the end effector may be further coupled to the second platform via a second gimbal.

In any of the above described devices the automated device may comprise a virtual Remote Center of Motion located at a selected entry point on the body of the subject.

The previously described devices may further comprise a base adapted for securing to the body of the subject. In the latter case, the base may comprise a printed circuit board, and the automated device may further comprise at least one electrical wire configured to connect the printed circuit board to at least one additional printed circuit board coupled to one or more of the first, second and third platforms. The one or more of the at least one electrical wires may then comprise a flat flex cable.

Yet other implementations may involve an automated device according to any of the above mentioned implementations, further comprising one or more sensors configured to be coupled to one or more of the first platform, the second platform, the third platform, the first piston, the second piston and the end effector. In such a case, at least a first sensor of the one or more sensors may be configured to measure a parameter associated with the interaction between the medical tool and a bodily tissue. In that case, the at least first sensor of the one or more sensors may be configured to measure a parameter associated with the interaction between the medical tool and a bodily tissue. The first sensor may be a force sensor.

In any of the above described automated devices comprising sensors, at least a second sensor of the one or more sensors may be configured to monitor the movement of one or more of the first platform, the second platform, the third platform, the first piston and the second piston.

Implementations of the systems and devices described above may further include any of the features described in the present disclosure, including any of the features described hereinabove in relation to other system and device implementations.

It is to be understood that the terms proximal and distal as used in this disclosure have their usual meaning in the clinical arts, namely that proximal refers to the end of a device or object closest to the person or machine inserting or using the device or object and remote from the patient, while distal refers to the end of a device or object closest to the patient and remote from the person or machine inserting or using the device or object.

It is also to be understood that although some examples used throughout this disclosure relate to systems and methods for insertion of a needle into a subject's body, this is done for simplicity reasons alone, and the scope of this disclosure is not meant to be limited to insertion of a needle into the subject's body, but is understood to include insertion of any medical tool into the subject's body for diagnostic and/or therapeutic purposes, including a port, introducer, catheter (e.g., ablation catheter), cannula, surgical tool, fluid delivery tool, or any other such insertable tool.

In addition, the terms "user", "doctor", "physician", "clinician", "technician", "medical personnel" and "medical staff" are used interchangeably throughout this disclosure and may refer to any person taking part in the performed medical procedure.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

DETAILED DESCRIPTION

Figure 1:
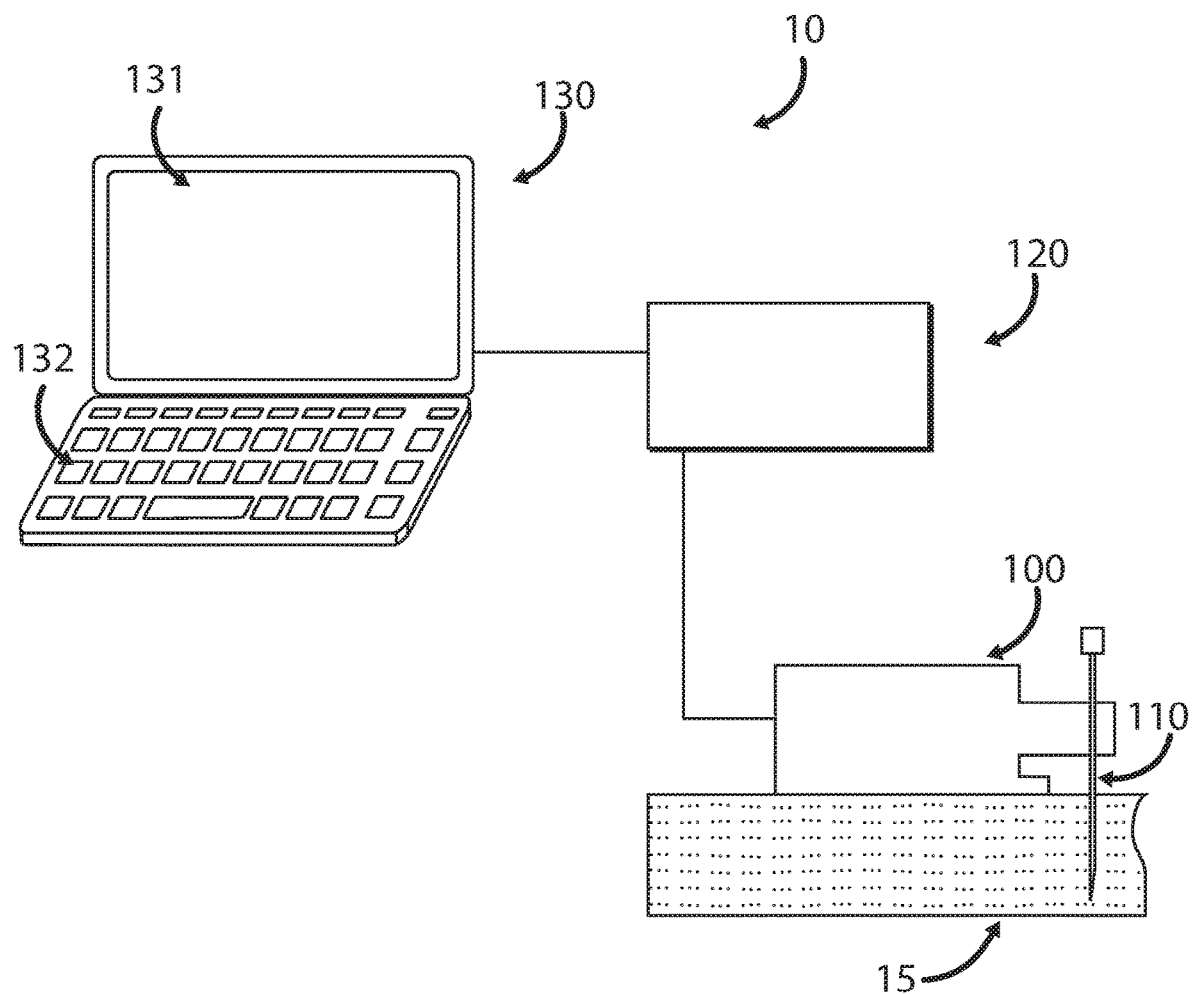
FIG. 1 shows a schematic diagram of an exemplary system for inserting a medical tool into the body of a subject.

FIG. 1 shows a schematic diagram of a system 10 for inserting a medical tool (e.g., needle) 110 into the body 15 of a subject. The system includes an automated insertion device 100, configured for steering the needle during its insertion into the subject's body 15. The needle 110 may be removably coupleable to the insertion device 100, such that the insertion device 100 can be used repeatedly with new needles.

In some implementations, the system 10 may be configured to operate in conjunction with an imaging system, such that the insertion procedure is image-guided. The utilized imaging modality may be any one of X-ray fluoroscopy, CT, cone beam CT, CT fluoroscopy, MRI, ultrasound, or any other suitable imaging modality.

The insertion device 100 may be configured to be mounted directly on the subject's body 15, as shown in FIG. 1, or it may be configured to be coupled to a dedicated arm or base which is secured to the patient's bed, to a cart positioned adjacent the patient's bed or to the imaging device, as described, for example, in abovementioned U.S. patent application Ser. No. 15/027,438, and in U.S. patent application Ser. No. 15/027,439, to Glozman et al, for "Gripper for Robotic Image Guided Needle Insertion", both of which are incorporated herein by reference in their entireties.

The system 10 further comprises a computer 130, including at least one processor (not shown) for image processing, calculation of the optimal needle insertion path, etc., and a display 131 on which the obtained images, the calculated insertion path, etc., can be displayed. The computer 130 may be a personal computer (PC), a laptop, a tablet, a smartphone or any other processor-based device. The computer 130 may also include a user interface 132, which may be in the form of buttons, switches, keys, keyboard, computer mouse, joystick, touch-sensitive screen, etc. The display 131 and user interface 132 may be two separate components, or they may form together a single component, such as a touch-sensitive screen ("touch screen").

The computer 130 may be configured, inter alia, to receive, process and visualize on the display 131 images obtained from the imaging system (in DICOM format, for example), to calculate the optimal pathway for the medical tool, and to control needle steering, which may be executed in a closed-loop manner, i.e., the processor may generate motion commands to the insertion device 100 via the controller 120 and receive feedback regarding the actual location of the tool, which is then used for real-time pathway corrections. In some implementations, the optimal pathway may be calculated based on input from the user, such as the entry point, target and areas to avoid en route (also referred to as "obstacles"), which the user marks on at least one of the obtained images. In other implementations, the processor may be further configured to identify and mark the target, the obstacles and the optimal entry point. The optimal pathway may be calculated in a two-dimensional plane or in a three-dimensional space. In some implementations the needle path may be calculated in a two-dimensional plane, however, due to tissue movement, for example, the planned path cannot be followed and it is also not possible to adjust the needle path such that it remains in the same plane on which the original path was calculated, such that the real-time pathway corrections are executed in the three-dimensional space.

The system 10 further includes a controller 120, e.g., a robot controller, which controls the movement of the insertion device 100 and the steering of the medical tool 110 towards the target (e.g., lesion or tumor) within the subject's body 15. Depending on the planned trajectory, needle steering may be carried out in a two-dimensional plane or in a three-dimensional space. In some implementations, the controller 120 may be further configured to control the operation of sensors (not shown), such as a force sensor and/or an acceleration sensor, implemented in the system 10. Use of sensor/s for sensing parameters associated with the interaction between a medical tool and a bodily tissue, e.g., a force sensor, and utilizing the sensor data for guiding the insertion of the medical tool and/or for initiating imaging, is described, for example, in co-owned International Patent Application No. PCT/IL2016/051013 to Shochat et al, for "Systems and Methods for Guiding Insertion of a Medical Tool", incorporated herein by reference in its entirety.

The controller 120 may be a separate component, as shown in FIG. 1. Alternatively, at least a portion of the controller 120 may be embedded within the insertion device 100, and/or within the computer 130.

Figure 2:
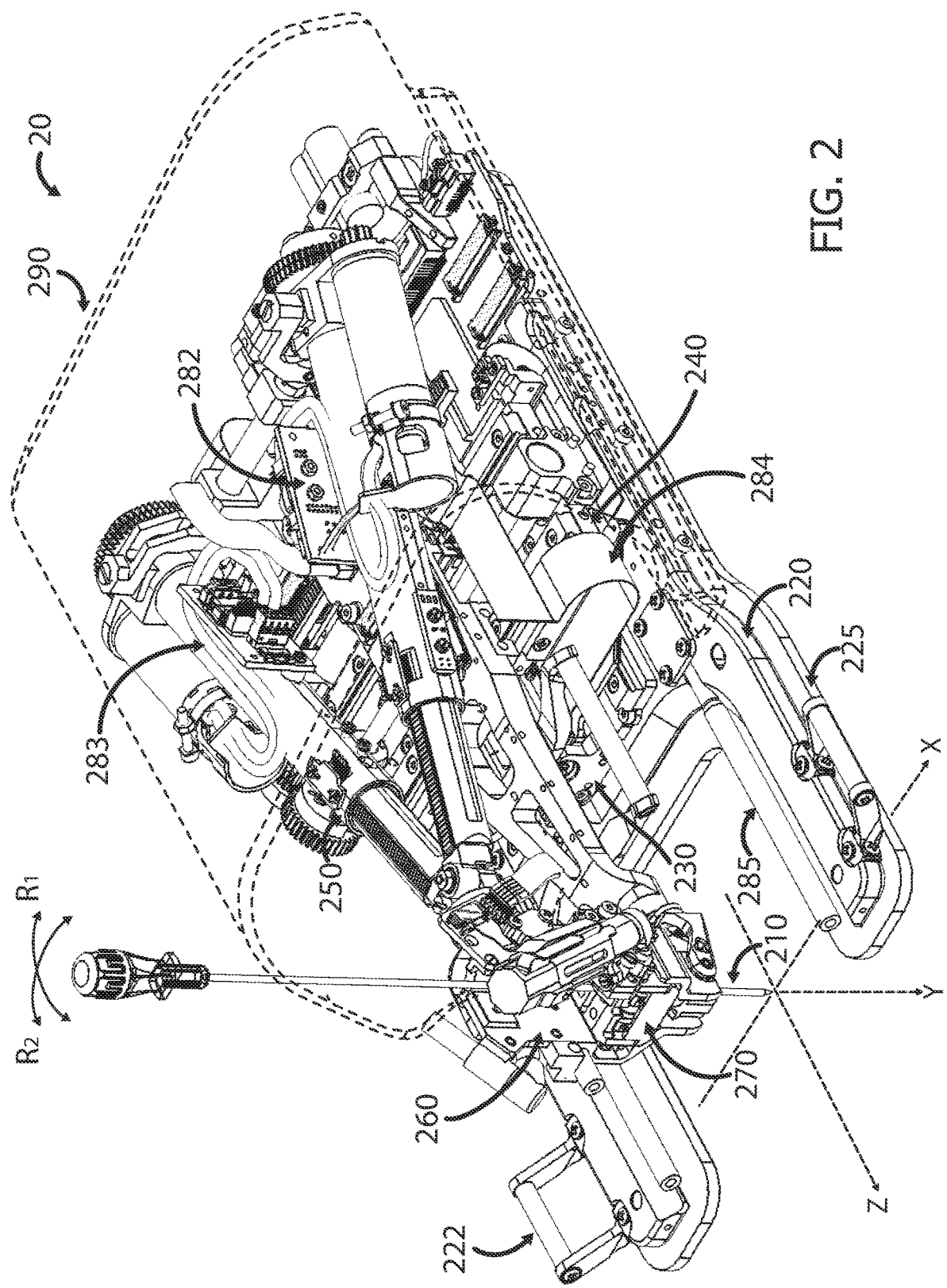
FIG. 2 shows a perspective view of an exemplary automated insertion device.

FIG. 2 shows a perspective view of an exemplary automated insertion device 20 having five degrees of freedom (DOF): linear translation along the Z axis (front-back) provided by a Z platform 230, linear translation along the X axis (left-right) provided by an X platform 240, rotation about the X axis (forward-backward) $R_1$, rotation about the Z axis (left-right) $R_2$, both rotations provided by a top assembly 250, and insertion, i.e., longitudinal needle translation along the Y axis, provided by an insertion mechanism. The insertion mechanism may be part of an end effector (EEFF) 260, an insertion module (IM) 270 coupled to the EEFF, or divided between the EEFF and the IM, as will be explained in detail below.

The insertion device 20 may further comprise a base 220. In some implementations, the insertion device 20 may be attached to the subject's body directly, and accordingly, the base 220 may be provided with straps (not shown in FIG. 2) and handles (or anchors) 222 for connecting the straps to the base, with an adhesive layer (not shown) on the bottom surface of the base 220, or with any other suitable means for attaching the base to the subject's body. In other implementations, the insertion device 20 may be attached to the subject's body via a dedicated mounting pad 225. The mounting pad 225 may be attached to the bottom of the device base 220 or to the bottom of a sterile drape (not shown in FIG. 2) which is used to cover the insertion device 20, at least in part, or it may be positioned on the subject's body first and then the insertion device 20, or more specifically—the base 220 of the insertion device, is coupled to the mounting pad. The mounting pad may be configured as a cushion, for example, to minimize any discomfort to the patient resulting from attachment of the insertion device to his/her body. In some implementations, if the insertion procedure is image guided, the mounting pad 225 may include one or more fiducial markers (not shown), which form together an adjustable registration frame for determining the insertion device's position at any point during the procedure if the device 20 outside the scanned volume, as described, for example, in co-owned International Patent Application No. PCT/IL2016/051396 to Roth et al, for "Adjustable Registration Frame", which is hereby incorporated by reference in its entirety. In further implementations, the insertion device 20 may be attached to the subject's body by coupling the device to a dedicated mounting base (or cradle) (not shown). Exemplary attachment devices are disclosed in co-owned U.S. International Patent Application No. PCT/IL2017/050430 to Arnold et al, for "Devices and Methods for Attaching a Medical Device to a Subject", which is hereby incorporated by reference in its entirety.

The insertion device 20 may further include at least one Printed Circuit Board (PCB) 282 and electrical cables/wires 283 to provide electrical connection between the controller and the motors and other electronic components of the insertion device. In some implementations, at least one of the electrical cables may be configured as a Flexible Flat Cable (FFC), e.g., FFC 284. Such a cable takes up less space and provides greater flexibility and easier cable management. Further, in some implementation, a single FFC may be used to provide electrical connection between remote electronic components of the insertion device. In such a case, FFC 284, for example, may be folded and bent multiple times between the different platforms of the device 20, to electronically connect the base 220 with the top assembly 250. Thus, a single FFC 284 may be used instead of numerous round cables, eliminating wire coupling issues, taking up less space, and providing the flexibility required in a complex insertion device having several bases/platforms, each moving in a different direction.

The insertion device 20 may further include fiducial markers (or registration elements) 285 disposed at specific locations on the device, for registration of the device to the image space, in image guided procedures.

In some implementations, the insertion device 20 may include a housing (or cover) 290, which covers and protects, at least partially, the mechanical and electronic components of the device 20 from being damaged or otherwise compromised.

Figure 3:
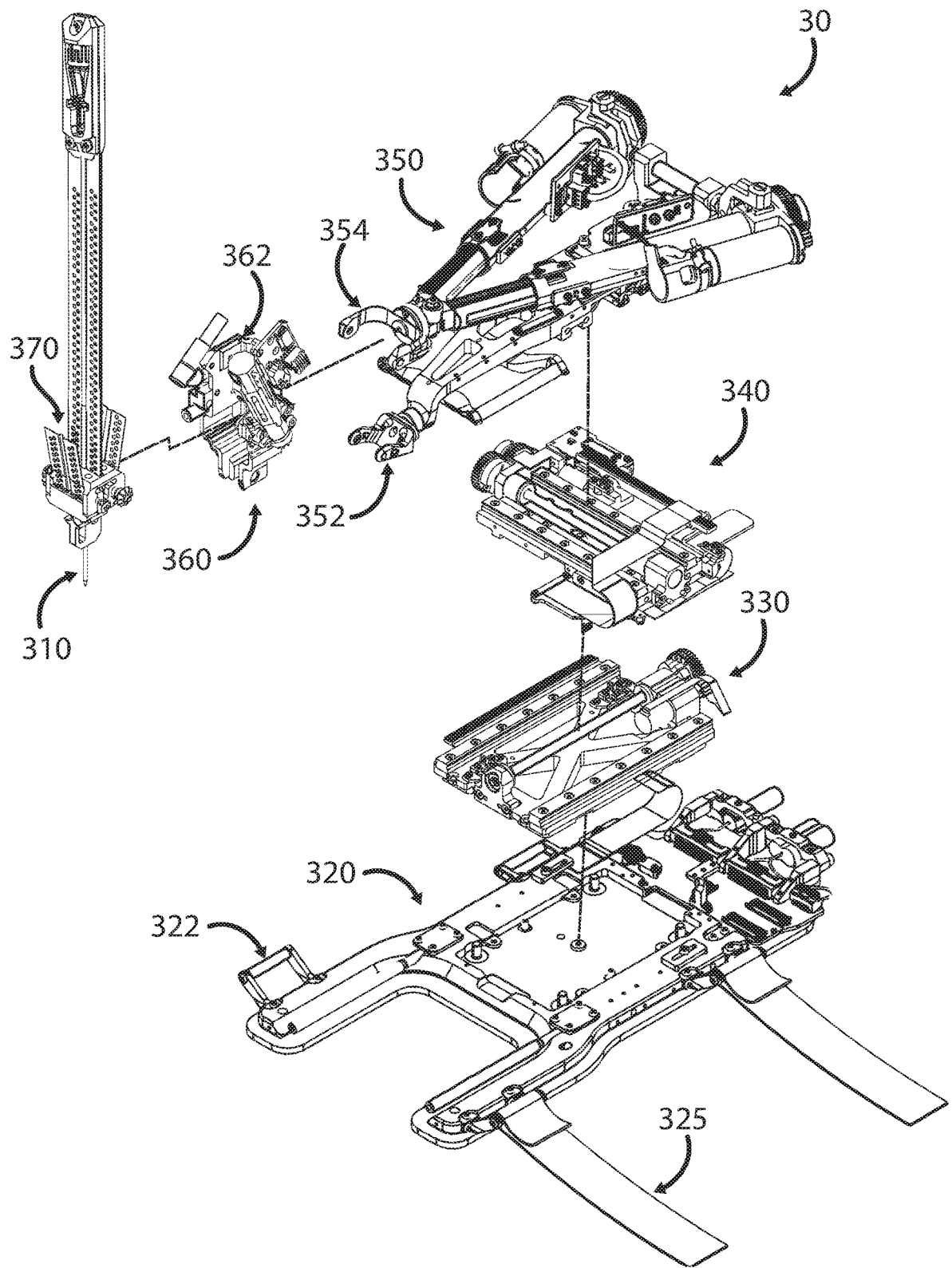
FIG. 3 shows an exploded view of an exemplary automated insertion device.

FIG. 3 is an exploded view of the exemplary insertion device 20 of FIG. 2, designated by numeral 30 in FIG. 3, showing the device base 320, the Z platform 330, the X platform 340, the top assembly 350, the end effector 360 and the insertion module 370. In some implementations, the device base 320 may include at least part of the mechanism for attaching the insertion device 30 to the subject's body, such as one or more strap anchors 322 to which one or more straps 325 are coupled by the user, or the straps 325 themselves, which may be provided together with the base 320. In some implementations, the device's cover (not shown in FIG. 3) may also include at least part of the attachment mechanism, such as the strap anchors. The Z platform 330 may be coupled to the device base 320 (e.g., using screws), and it may include at least part of the mechanism which enables the X platform 340 to move linearly along the Z axis on top of the Z platform 330. The X platform 340 may include the complimentary part of the mechanism which enables it to move linearly along the Z axis, as well as at least part of the mechanism which enables the top assembly 350 to move linearly along the X axis on top of the X platform 340. The top assembly 350 may include the complimentary part of the mechanism which enables it to move linearly along the X axis, and it may further include the mechanism which enables the end effector 360 to rotate. In some implementations, the end effector 360 may be coupled to the top assembly via one or more gimbals 352 and 354. The end effector 360 may include a housing (or—frame) 362 for receiving the insertion module 370, and it may further include at least part of the insertion mechanism, as will be explained in detail below. The insertion module 370 may include the insertion mechanism in its entirety, or the complimentary part of the insertion mechanism, in case the end effector 360 includes part of the insertion mechanism, and it may further include the medical tool 310 to be inserted into the subject's body. Such a medical tool may be a needle (e.g., a biopsy needle), an introducer, a catheter etc. In some implementations, the medical tool 310 may be integral with the insertion module 370. In other implementations, the medical tool 310 may be separate from the insertion module 370, such that it is coupled to the insertion module 370 by a member of the medical staff prior to commencing the insertion procedure.

Figure 4:
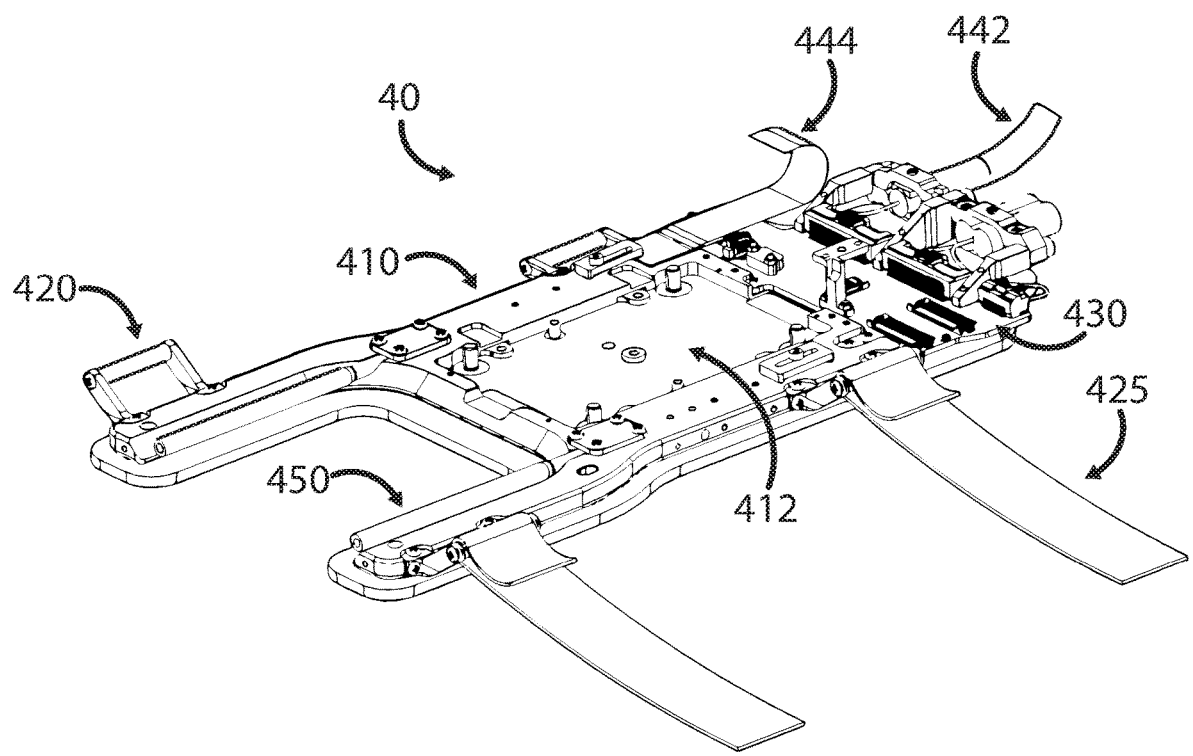
FIG. 4 shows a perspective view of an exemplary insertion device base.

FIG. 4 shows a perspective view of an exemplary device base 40. The base may include a base plate 410 for attaching to the subject's body, either directly or via a dedicated mounting pad or a mounting base (both not shown in FIG. 4). The base plate 410 may include a dedicated area, such as in the form of a depression 412, for receiving and coupling thereto the Z platform (not shown in FIG. 4). The device base 40 may further include a plurality of anchors 420 to which straps/belts 425 may be coupled to secure the base 40 (and thus the insertion device) to the subject's body. Alternatively, the straps/belts 425 may be coupled to a mounting pad or mounting base to which the insertion device is then coupled. The device base 40 may further include at least one Printed Circuit Board (PCB) 430, which accommodates a plurality of the device's electronic components, such as a CPU, and electrical wires, some of which provide an electrical connection between the base PCB 430 and external components, such as cable 442 which may connect the base PCB 430 to the controller (not shown in FIG. 4), and some of which connect between the base PCB 430 and other electronic components of the insertion device, such as FFC 444 which provides electrical connection between the base PCB 430 and the X platform PCB (not shown in FIG. 4).

The device base 40 may further include one or more registration elements, such as fiducial markers 450, which are utilized in the process of registering the insertion device to the image space, in image guided procedures.

Figure 5:
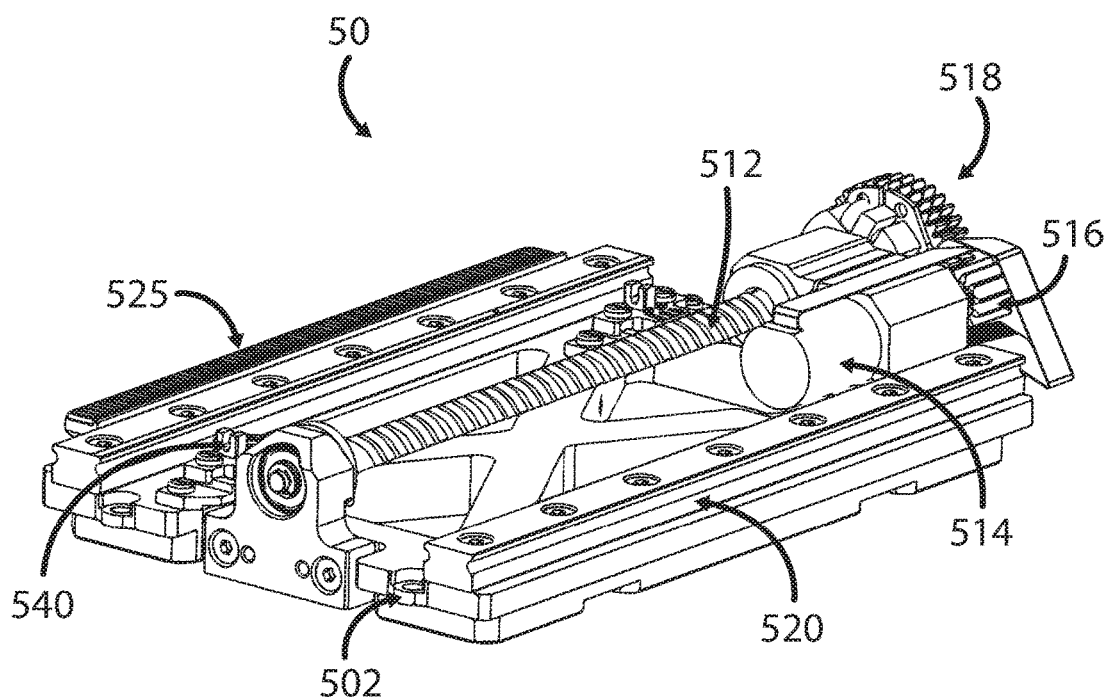
FIG. 5 shows a perspective view of an exemplary robotic platform of an automated insertion device.

FIG. 5 shows a perspective view of an exemplary Z platform 50 of the insertion device. The Z platform 50 may be coupled to the device base (not shown in FIG. 5), such as by using a plurality of screws (not shown) and corresponding sockets 502, and it may include at least part of the driving mechanism which enables movement of the X platform (not shown in FIG. 5) on top of the Z platform 50 and along the Z axis. In some implementations, the driving mechanism may include a ball screw (or—lead screw) mechanism. It can be appreciated that a ball screw mechanism is merely one example of a mechanism to propel the X platform along the Z axis, and other suitable propulsion mechanisms may be implemented instead or in addition.

In some implementations, the Z platform 50 may include a threaded shaft 512, which is rotated by a motor 514 (e.g., a brushless electric motor) via a pinion 516 and gear 518, and the X platform may include, coupled to its bottom surface, an internally threaded nut (not shown in FIG. 5), such that the rotation of the threaded shaft 512 is transformed into linear movement of the nut and therefore to linear movement of the X platform along the Z axis. In some implementations, the threaded shaft and nut may be provided preassembled as an integral unit, and the X platform may be secured to the threaded nut only after the preassembled shaft and nut (i.e., the ball screw mechanism) are secured to the Z platform. However, it should be noted, that in the present disclosure the shaft 512 is referred to as being part of the Z platform 50 and the nut is referred to as being part of the X platform, since the shaft remains stationary (though it does rotate) on the Z platform, whereas the nut moves together with the X platform, as one piece.

The motor 514 may be provided with a rotational encoder, such as rotational magnetic encoder model IEM3-1024, manufactured by Faulhaber of Schonaich, Germany. The encoder may be provided separately from the motor or it may be provided as an integral part of the motor such that both the motor and its encoder are designated by numeral 514.

The Z platform 50 may further include one or more rails 520 which guide the X platform's movement along the Z axis, e.g., via carriages (not shown in FIG. 5) which are attached to the bottom surface of the X platform and are configured to couple with the rails 520 such that they can move freely along the rails 520. A linear encoder, e.g., linear magnetic encoder model ID1101L manufactured by Posic Ltd. of Colombier, Switzerland, may be used to monitor the movement of the X platform along the Z axis. The encoder scale 525 may be positioned adjacent at least one of the rails 520, and the encoder reader (not shown in FIG. 5) may be coupled to the bottom portion of the X platform. A limit switch may also be utilized, in order to limit the travel of the X platform and prevent it from reaching the end of the rails, which may disrupt the proper function of the insertion device or even cause damage to the X platform and/or the rails. The limit switch may include a sensor 540, such as an opto-coupler having a light (e.g., infrared) source and a light detector positioned opposite each other, near each end of at least one of the rails 520, and at least one sensor flag (not shown in FIG. 5) coupled to the bottom surface of the X platform, such that when the flag passes between the light source and a light detector and blocks the emitted light from reaching the light detector, an alert may be prompted and/or the movement of the X platform may be automatically stopped. It can be appreciated that the limit switch implemented in the disclosed device is not limited to an optical sensor, and other types of limit switches, such as limit switches based on proximity sensors (magnetic field, capacitance, etc.) may also be used.

Figure 6A:
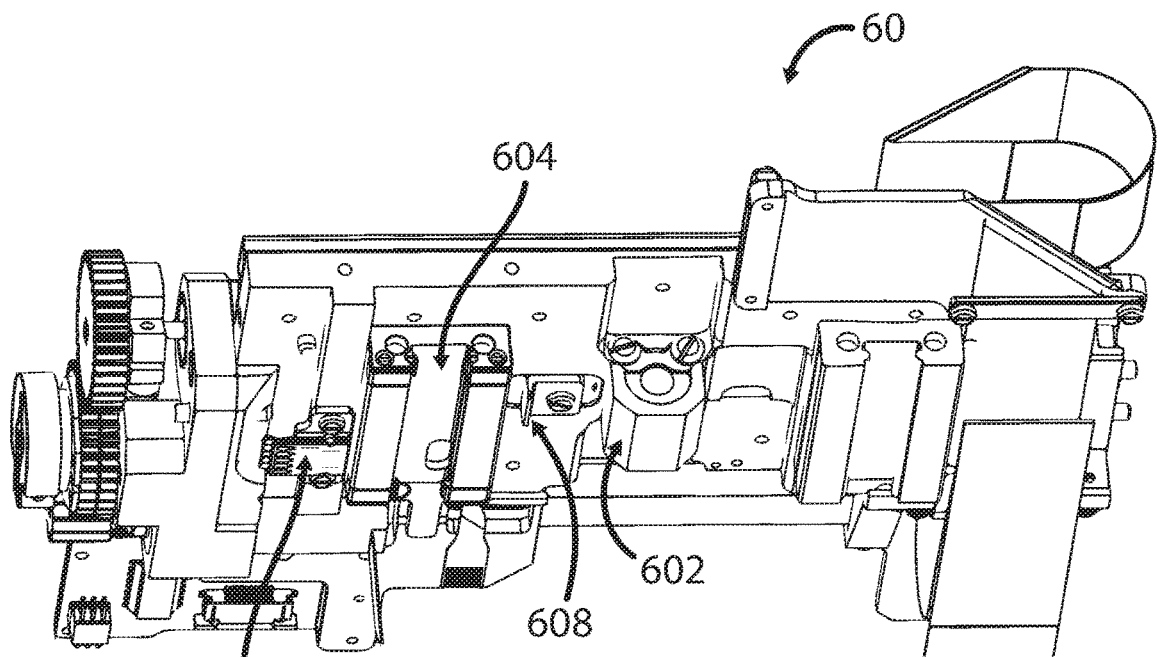
FIGS. 6A-6B show perspective views of another exemplary robotic platform of an automated insertion device.

FIG. 6A shows a bottom perspective view of an exemplary X platform 60 of the insertion device. The X platform 60 may include, coupled to its bottom surface, the internally threaded nut 602, which mates with the threaded shaft of the Z platform. Rotation of the threaded shaft by the motor and gears of the Z platform is transformed into linear movement of the nut 602 and therefore of the X platform 60 along the Z axis. Also shown are the carriages 604 which mate with and slide along the rails of the Z platform so as to guide and direct the linear movement of the X platform 60 along the Z axis. The X platform 60 may further include, coupled to its bottom surface, the linear encoder reader 606, which operates in conjunction with the Z platform's encoder scale (not shown in FIG. 6A) to monitor the movement of the X platform 60 along the Z axis, and the limit switch flag 608, which operates in conjunction with the Z platform's limit switch sensor (not shown in FIG. 6A) to limit the travel of the X platform and prevent it from reaching the end of the Z platform's rails.

Figure 6B:
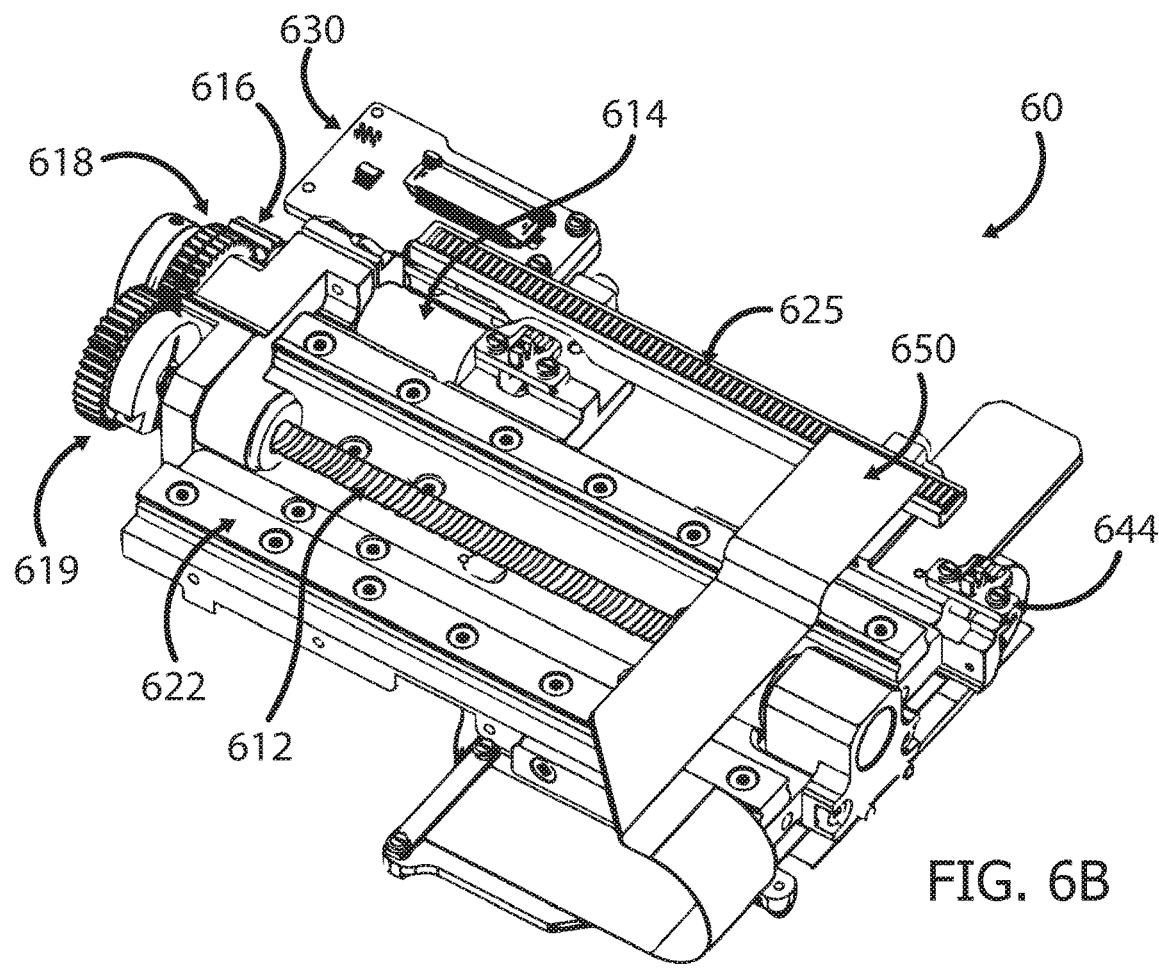

FIG. 6B shows a top perspective view of the X platform 60. The X platform 60 may include at least part of the driving mechanism which enables movement of the top assembly (not shown in FIG. 6B) on top of the X platform 60 and along the X axis. In some implementations, the driving mechanism may include a ball screw (or—lead screw) mechanism. It can be appreciated that a ball screw mechanism is merely one example of a mechanism to propel the top assembly along the X axis, and other suitable propulsion mechanisms may be implemented instead or in addition.

In some implementations, the X platform 60 may include a threaded shaft 612, which is rotated by a motor 614 (e.g., a brushless electric motor) via a pinion 616 and one or more gears 618 and 619, and the top assembly may include, coupled to its bottom surface, an internally threaded nut (not shown in FIG. 6B), such that the rotation of the threaded shaft 612 is transformed into linear movement of the nut and therefore of the top assembly along the X axis. In some implementations, the threaded shaft and the internally threaded nut may be provided preassembled as an integral unit, and the top assembly may be secured to the threaded nut after the preassembled shaft and nut (i.e., the ball screw mechanism) is secured to the X platform. However, it should be noted, that in the present disclosure the shaft 612 is referred to as being part of the X platform 60 and the nut is referred to as being part of the top assembly, since the shaft 612 moves together with the X platform, as one piece, and the nut moves together with the top assembly, as one piece.

The motor 614 may be provided with a rotational encoder, such as rotational magnetic encoder model IEM3-1024, manufactured by Faulhaber of Schonaich, Germany. The encoder may be separate from the motor or it may be provided integrally with the motor such that both the motor and its encoder are designated by numeral 614.

The X platform 60 may further include one or more rails 622 which guide the top assembly's movement along the X axis, e.g., via carriages (not shown in FIG. 6B) which are attached to the bottom surface of the top assembly and are configured to couple with the rails 622 such that they can move freely along the rails 622.

The combination of the Z and X platforms enables full planar movement of the top assembly.

A linear encoder, such as linear magnetic encoder model ID1101L, manufactured by Posic Ltd. of Colombier, Switzerland, may be used to monitor the movement of the top assembly along the X axis. The encoder scale 625 may be positioned adjacent at least one of the rails 622, and the encoder reader (not shown in FIG. 6B) may be coupled to the bottom portion of the top assembly. A limit switch may also be utilized, in order to limit the travel of the top assembly and prevent it from reaching the end of the rails 622, which may disrupt the proper function of the insertion device or even cause damage to the top assembly and/or the rails 622. The limit switch may include a sensor 644, such as an opto-coupler having a light source and a light detector positioned opposite each other, positioned near each end of at least one of the rails 622, and at least one sensor flag (not shown in FIG. 6B) coupled to the bottom surface of the top assembly. It can be appreciated that the limit switch implemented in the disclosed device is not limited to an optical sensor, and other types of limit switches, such as limit switches based on proximity sensors (magnetic field, capacitance, etc.) may alternatively be used.

The X platform 60 may further include at least one PCB 630 which accommodates a plurality of the X platform's electronic components, and electrical wires. In some implementations, FFC 650, which provides electrical connection between the PCB of the device base and the PCB of the top assembly, may be mechanically coupled to the X platform 60.

Figure 7A:
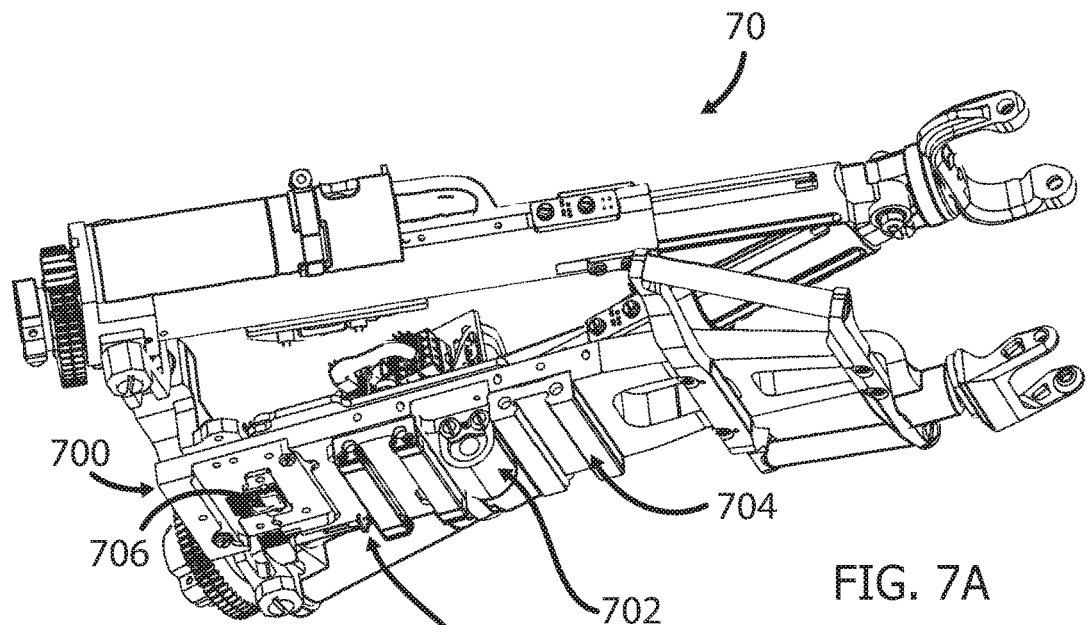
FIGS. 7A-7B show perspective views of an exemplary top assembly of an automated insertion device.

FIG. 7A shows a bottom perspective view of an exemplary top assembly 70 of the insertion device. The top assembly 70 may include a base 700 to the bottom surface of which the internally threaded nut 702, which mates with the threaded shaft of the X platform, is coupled. Rotation of the threaded shaft by the motor and gears of the X platform is transformed into linear movement of the nut 702 and therefore of the top base 700 and the entire top assembly 70 along the X axis. Also shown are the carriages 704 which mate with and slide along the rails of the X platform, so as to guide and direct the linear movement of the top assembly 70 along the X axis. The top assembly 70 may further include, coupled to its bottom surface, the linear encoder reader 706, which operates in conjunction with the X platform's encoder scale (not shown in FIG. 7A) to monitor the movement of the top assembly 70 along the X axis, and the limit switch flag 708, which operates in conjunction with the X platform's limit switch sensor (not shown in FIG. 7A) to limit the travel of the top assembly 70 and prevent it from reaching the end of the X platform's rails.

Figure 7C:
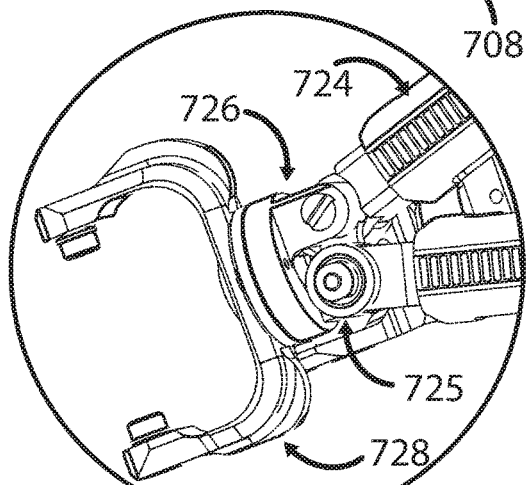
FIG. 7C shows a top view of a common joint to which the pistons of the top assembly of FIGS. 7A-7B are coupled.
Figure 7B:
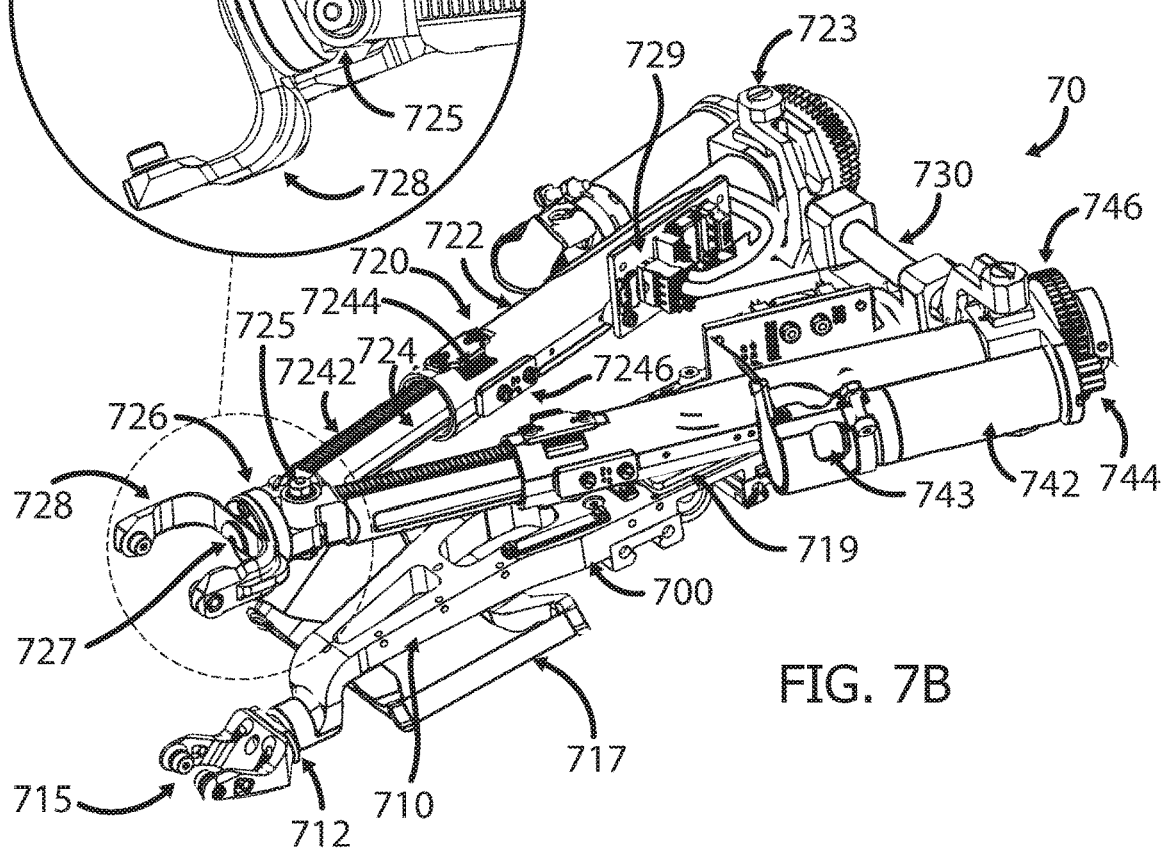

FIG. 7B shows a top perspective view of the top assembly 70. The top assembly 70 may include a base portion 700 and an arm member 710 extending from the base portion 700. The extending arm 710 may include, coupled to its distal end, a bottom gimbal 715, to which the device's end effector (not shown in FIG. 7B) is coupled. The bottom gimbal 715 may be coupled to the arm member 710 via an axial joint 712, to allow rotation of the gimbal 715, and thus of the end effector, while the arm 710 maintains its angular position. In some implementations, the top assembly arm 710 may include, coupled thereto, at least one registration element 717, which is utilized in the process of registering the insertion device to the image space, in image guided procedures. The registration elements 717 may comprise tubes (or—rods) made of carbon, for example. In some implementations, the top assembly 70 may further include a force sensor (not shown) attached to the arm member 710, for example, for measuring the forces exerted on the medical tool during its insertion into the subject's body. The real-time measurements of the force sensor may provide one or more of: a gating function, i.e., they may be used to define the optimal times/stages for initiating imaging of the region of interest, a monitoring and guidance function, i.e., they may be used to monitor the progress of the insertion procedure and assist in verifying that the needle is following its preplanned trajectory, and a safety function, i.e., they may be used to alert the clinician, and preferably also prompt automatic halt of the insertion procedure, upon detecting that needle has hit/entered an obstacle, such as a bone, a blood vessel, or the like, all as described in abovementioned International Patent Application No. PCT/IL2016/051013.

The top assembly 70 may further include piston mechanisms 720, positioned above the top assembly's base portion 700 and arm member 710. The arm member 710 and the piston mechanisms 720 distance the needle (not shown in FIG. 7B) from the metallic components of the device, such as the motors and the gears, and thus minimizes the occurrence of imaging artifacts in the area proximate the needle, which is scanned in order to follow and determine the position of the needle during the insertion procedure.

In some implementations, each piston mechanism 720 may include a cylinder 722 and a piston 724 which is moveable in and out of the cylinder 722, for example via a ball screw mechanism. It can be appreciated that a ball screw mechanism is merely one example of a mechanism to propel the piston in and out of the cylinder, and other suitable propulsion mechanisms may be implemented.

In some implementations, each piston mechanism 720 may include a motor 742, which rotates a threaded shaft (not shown in FIG. 7B) located within the cylinder 722, via a pinion 744 and a gear 746. The piston 724 may include at its proximal end, which is located within the cylinder 722, an internally threaded nut (not shown in FIG. 7B), which is operatively coupled to the threaded shaft, such that rotation of the threaded shaft is transformed into linear movement of the nut and therefore of the piston in and out of the cylinder 722, as required. The motor 742 may be provided with a rotational encoder 743 to monitor its rotation.

In some implementations, the distal end of each piston 724 may be coupled to a separate joint having at least two rotational DOFs, and both joints may be connected directly to the end effector (not shown in FIG. 7B). Such separate joints may be configured, for example, as ball-and-socket joints, as cardan joints, or as any other suitable joint. In other implementations, as shown from a perspective view in FIG. 7B and from a top view in FIG. 7C, the distal end joints 725 of the pistons 724 may be coupled to a common joint 726, which in turn is coupled to a top gimbal 728, to which the device's end effector (not shown in FIGS. 7B and 7C) is coupled, in addition to its coupling to the bottom gimbal 715. In such implementations, the distal end joints 725 may have one rotational DOF and the common joint 726 may have two rotational DOFs. Further, in such implementations, the distal end joints 725 of the pistons and the proximal end joints 723 of the cylinders, which may comprise cardan joints, for example, and provide each cylinder 722 with two DOFs, may be parallel to each other, such that the cylinders 722 and the pistons 724 may all be located on the same plane. An axial joint 727 connecting the top gimbal 728 to the common joint 726 allows the cylinders 722, the pistons 724 and the common joint 726 to all remain on the same plane as the top gimbal 728 with the coupled end effector are being rotated. The cylinders 722 and the pistons 724 all being located in a single plane allows also the horizontal axes of the cardan joints 723 of both cylinders 722 to be coupled to a single shaft (or—axle) 730, although in some implementations each cardan joint 723 may be coupled to a separate shaft. This configuration, in which the cylinders 722, the pistons 724, the common joint 726 and the shaft 730 are all located on the same plane, allows larger angular movement and thus a larger workspace of the end effector, without the limitations of ball-and-socket joints, for example, within a simple and compact design. It can be appreciated that although the top gimbal 728 and bottom gimbal 715 shown in FIGS. 7A-7C have two arms for coupling the end effector thereto, in some implementations either or both of the gimbals may have only one arm for coupling the end effector thereto, or they each may have any other suitable configuration suitable for coupling the end effector thereto.

The top assembly 70 may further include one or more PCBs, for example, a PCB 719 may be attached to the top assembly's base portion 700 and additional PCBs 729 may be coupled to each of the cylinders 722. Linear encoders, e.g., linear magnetic encoder model ID1101L manufactured by Posic Ltd. of Colombier, Switzerland, may be used to monitor the movement of the pistons 724 within the cylinders 722. The scales 7242 of the linear encoders may be coupled to the pistons 724, and the encoder readers 7244 may be coupled to the cylinders 722. Limit switches 7246 may also be utilized, in order to limit the travel of the piston 724 and prevent it from reaching the end of the threaded shaft.

Figure 7D:
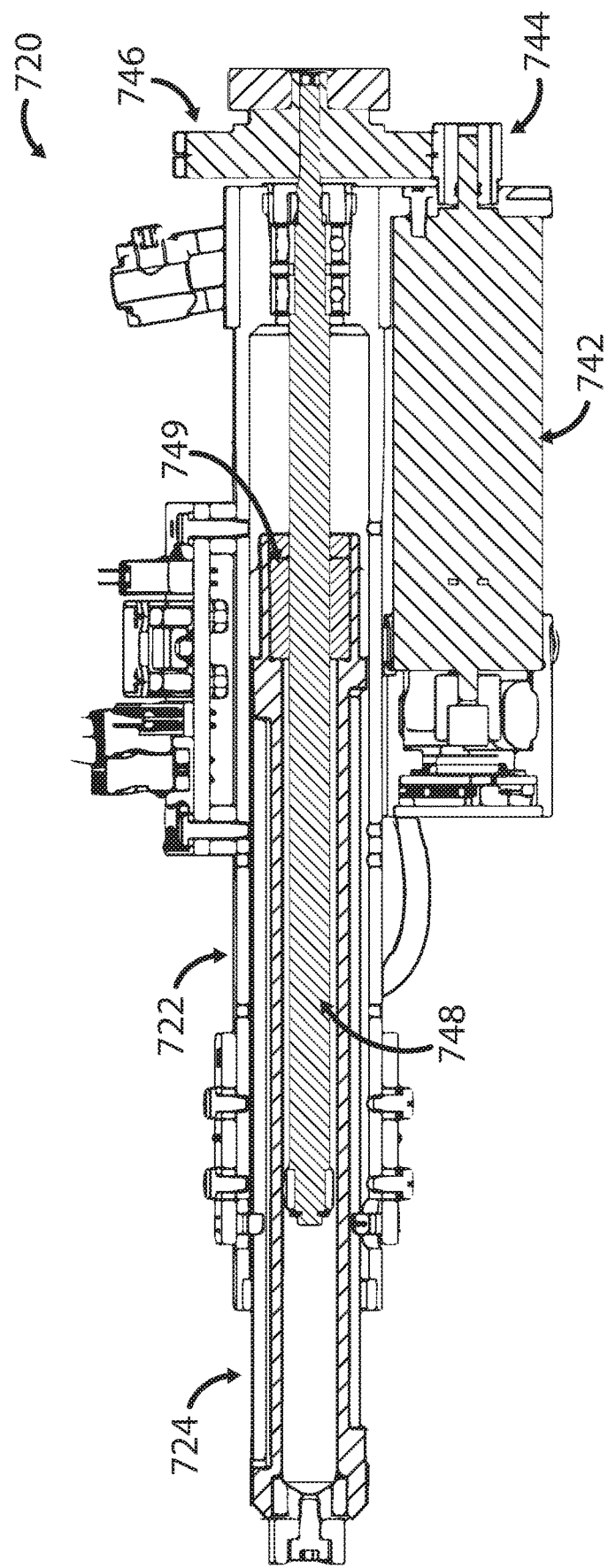
FIG. 7D shows a longitudinal cross-sectional view of a piston mechanism of the top assembly of FIGS. 7A-7B.

FIG. 7D shows a cross-sectional view of one of the piston mechanisms of FIGS. 7A-7B. As described above, each piston mechanism 720 may include a cylinder 722 and a piston 724 which is moveable in and out of the cylinder 722 via a ball screw mechanism. Each piston mechanism 720 may include a motor 742, which rotates a threaded shaft 748 located within the cylinder 722, via a pinion 744 and gear 746. The piston 724 may include at its proximal end, which is located within the cylinder 722, an internally threaded nut 749, which is operatively coupled to the threaded shaft 748, such that rotation of the threaded shaft 748 is transformed into linear movement of the nut 749, and thus of the piston 724, in and out of the cylinder 722.

Figure 8:
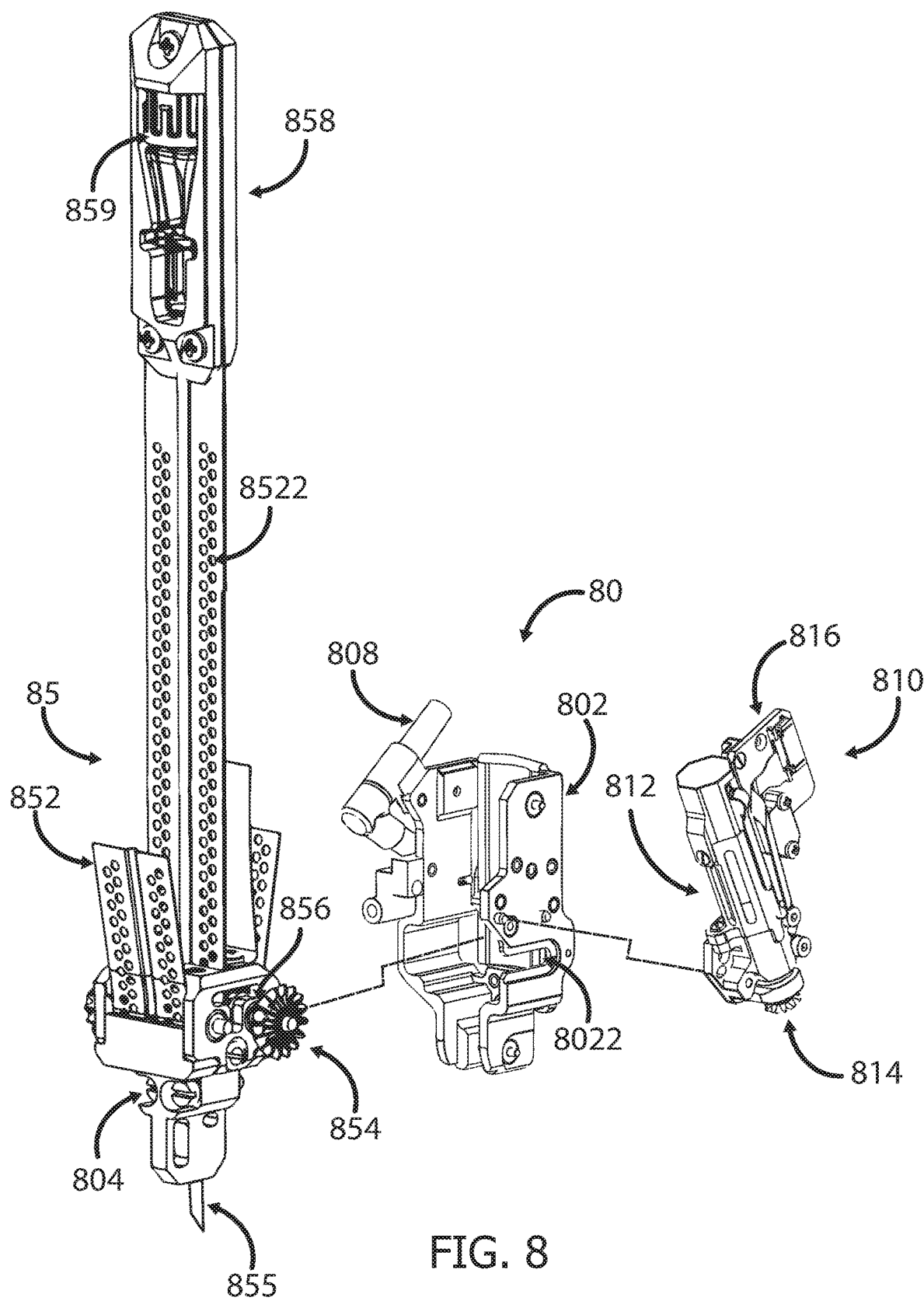
FIG. 8 shows an exploded view of an exemplary insertion assembly.

FIG. 8 shows an exploded view of an exemplary insertion assembly comprising an end effector 80 and an insertion module 85. The insertion module 85 may include two flexible strips 852 coupled together along their width, except in a region where they envelop the needle 855 at their center line. The flexible strips 852 may have perforations 8522 running along at least a portion of their length and on either side of the needle position along the centerline. The insertion module 85 may further include rollers (not shown) having protrusions, such that the perforations 8522 of the strips 852 engage with the protrusions on the rollers, and as the rollers counter-rotate in the appropriate direction, the double strip-needle assembly is forced in a distal direction, i.e., towards the patient's body. The strips 852 then peel away from the needle 855, and the needle 855 advances into the patient's body. The insertion module 85 may further include a needle head holder 858, which secures together the needle head 859 and the proximal end of the strips 852.

The end effector 80 may comprise a frame 802 for receiving the insertion module 85. Once inserted into the frame 802, the insertion module 85 may be locked therein using screws 804, for example, or any other suitable securing mechanism, such as snap-fit mechanism. The end effector 80 may further include a motor assembly 810, which may include a geared motor 812 (i.e., motor and planetary gear system) provided with a motor encoder (not shown), a bevel gear 814, and a PCB 816. The motor assembly 810 may actuate the insertion mechanism as follows: the geared motor 812 rotates the bevel gear 814, which in turn rotates a bevel gear 854 of the insertion module 85, to which it is coupled. The bevel gear 854 of the insertion module 85 then rotates the rollers of the insertion module 85, and the counter-rotation of the rollers pulls downwardly the coupled strips 852 via the "timing belt-like" mechanism comprised of the rollers' protrusions and the strips' perforations.

In some implementations, the end effector's frame 802 may include a dedicated slot 8022 for receiving the shaft 856 of the bevel gear 854 of the insertion module, such that the bevel gear 854 remains outside the frame 802 after the insertion module 85 is inserted therein, to enable its coupling to the bevel gear 812 of the end effector's motor assembly 810.

The end effector 80 may further include one or more registration elements 808, which may be coupled to its frame 802.

Further details and embodiments of the exemplary insertion assembly are disclosed in co-owned International Patent Application No. PCT/IL2015/051158, to Galili et al, for "Needle Insertion Guide", incorporated herein by reference in its entirety.

In some implementations, the insertion module 85 is a disposable single-use unit, and the end effector 80 is reusable, i.e., it can be used repeatedly with new disposable insertion modules 85. In such cases, the end effector 80 may be an integral unit of the insertion device. In other implementations, the end effector 80 may also be disposable and thus provided separately from the automated insertion device. In such cases the end effector 80 and the insertion module 85 may be provided as a single disposable unit.

Figure 9:
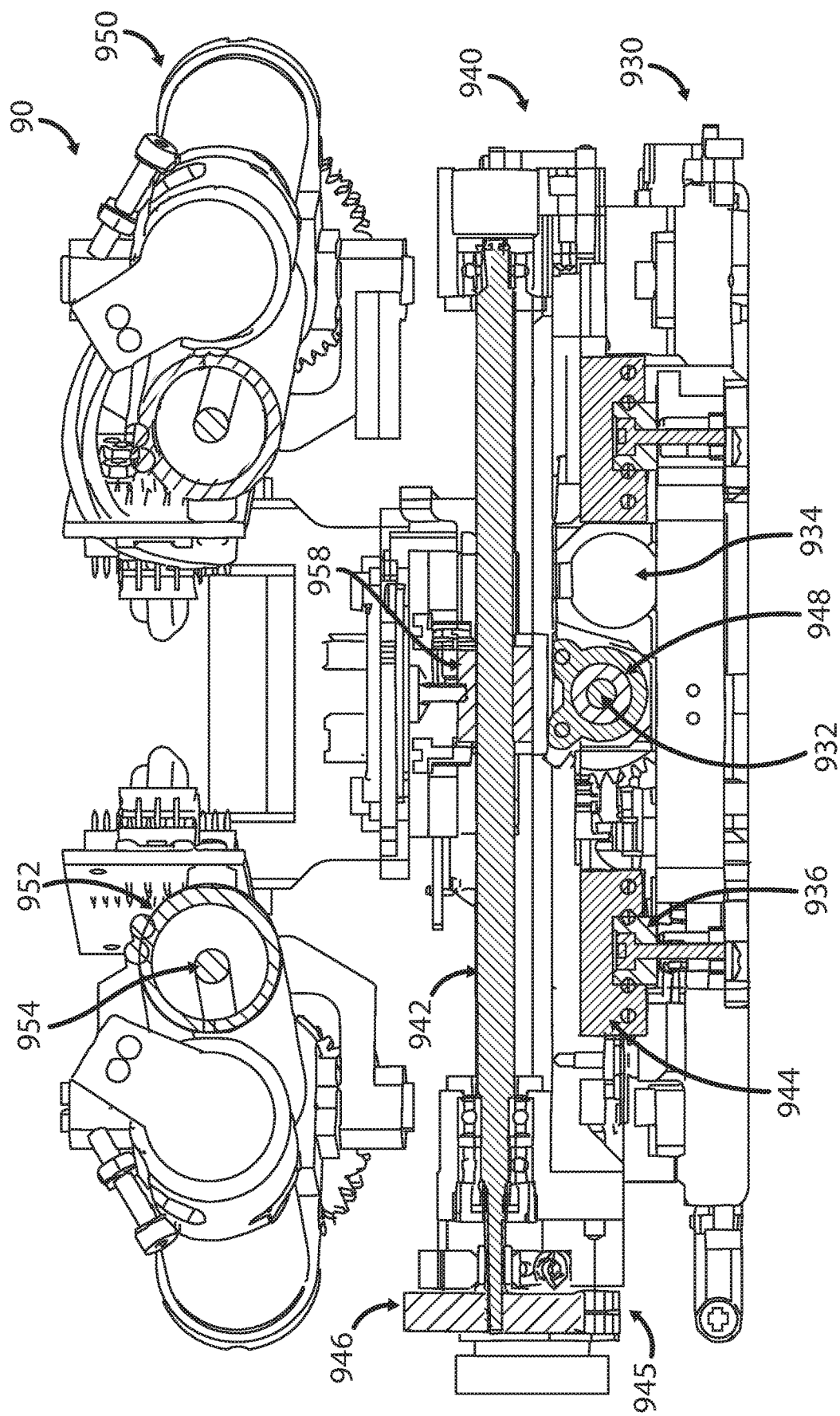
FIG. 9 shows a transverse cross-sectional view of an exemplary automated insertion device, demonstrating the interfaces between the different platforms.

FIG. 9 shows a transverse cross-sectional view of the insertion device 90, demonstrating the interfaces between the different platforms. As described hereinabove, the movement of both the X platform along the Z axis and the top assembly along the X axis may be propelled via a ball screw mechanism. In addition, the linear movement of both the X platform and the top assembly may be guided via a rail-carriage mechanism. Z-X platforms: The Z platform 930 may include a threaded shaft 932 and the X platform 940 may include an internally threaded nut 948 which is operatively coupled to the shaft 932. Rotation of the shaft 932 by a motor 934 and gear/s (not shown in FIG. 9) is transformed into linear movement of the nut 948, and therefore of the X platform 940, along the Z axis. Further, the Z platform 930 may include one or more rails 936 and the X platform 940 may include one or more corresponding carriages 944 which are operatively coupled to the rails 936 and can move freely (or—slide) along the rails 936, to guide the linear movement of the X platform along the Z axis.

X platform—top assembly: The X platform 940 includes a threaded shaft 942 and the top assembly 950 includes an internally threaded nut 958, which is operatively coupled to the shaft 942. Rotation of the shaft 942 by a motor (not shown in FIG. 9) and gears 945 and 946 is transformed into linear movement of the nut 958, and therefore of the top assembly 950, along the X axis. Further, the X platform 940 may include one or more rails (not shown in FIG. 9) and the top assembly 950 may include one or more corresponding carriages (not shown in FIG. 9), which are operatively coupled to the rails and can move freely (or—slide) along the rails, to guide the linear movement of the top assembly along the X axis. Also shown in FIG. 9 are the top assembly's cylinders 952 with the threaded shafts 954 positioned therein.

FIGS. 10A-10D show the top assembly 1000 in four different states depicting an exemplary rotation range of the insertion assembly, i.e., the EEFF and the IM, of the device.

Figure 10A:
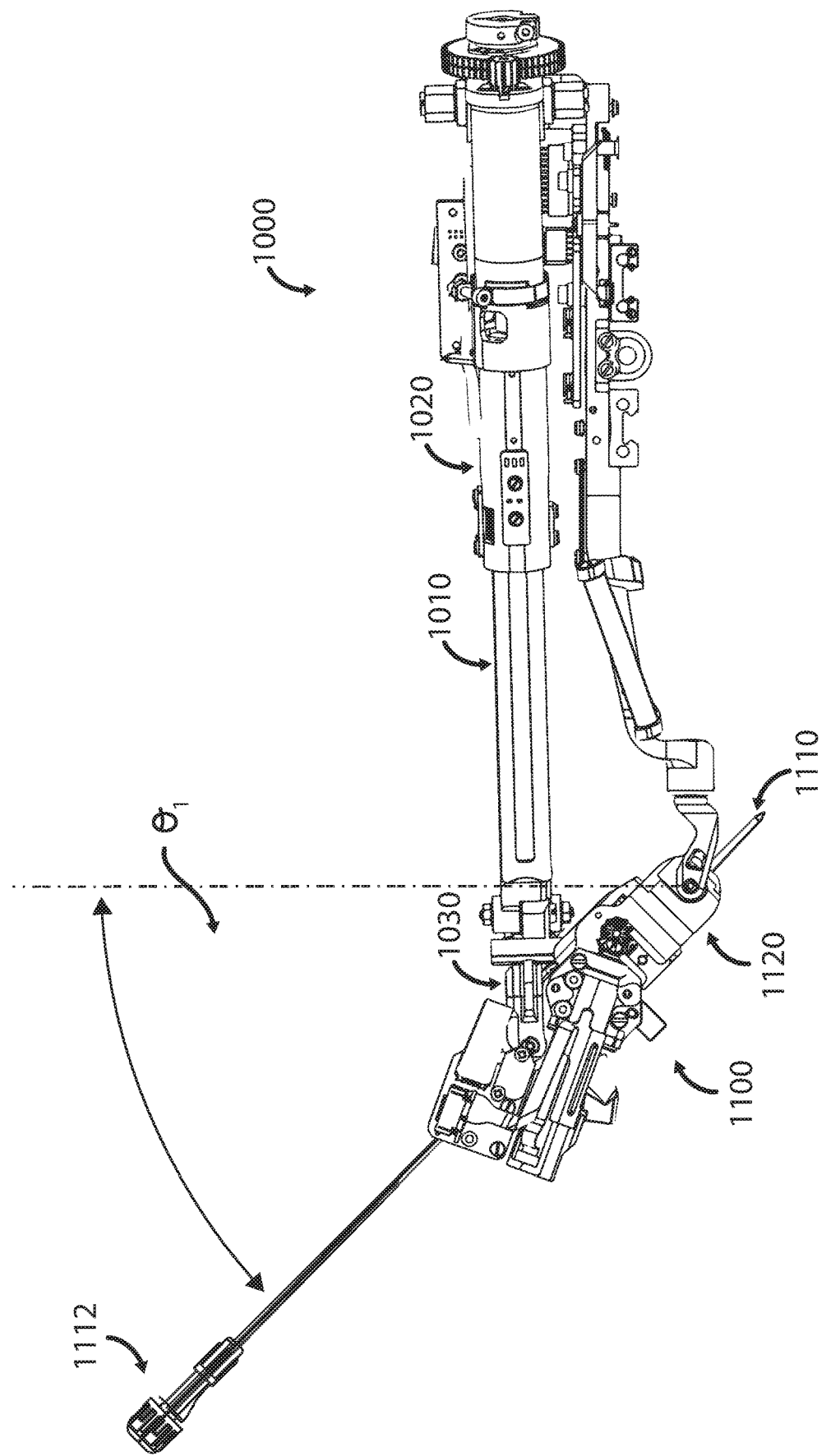
FIGS. 10A-10E depict an exemplary rotation range of an insertion assembly.

FIG. 10A shows a side view of the top assembly 1000 with the insertion assembly 1100 at its maximal backward-directed rotation angle $\theta_1$, i.e., the insertion assembly 1100 is maximally rotated about the X axis away from the device. A backward angle is achieved by propelling both pistons 1010 forward, out of the cylinders 1020, causing the needle head 1112 to rotate forward and the needle tip 1110 to point backward, i.e., toward the device. As shown, the manipulation of the needle, both its rotation and its insertion, is carried out at the coupling point/s of the top gimbal 1030 and the EEFF 1120, close to the patient's body, unlike prior art systems which generally manipulate the needle at the needle head. Since there is no need to generate the motion required for rotation and insertion of the full length of the needle, which could be considerable, the workspace required by the disclosed insertion system is significantly smaller than that of prior art systems. Further, the devices of this disclosure are capable of driving needles of variable lengths while the dimensions and workspace of the driving mechanism do not depend on the length of the needles, as described in above-mentioned U.S. patent application Ser. No. 15/027,438.

Figure 10B:
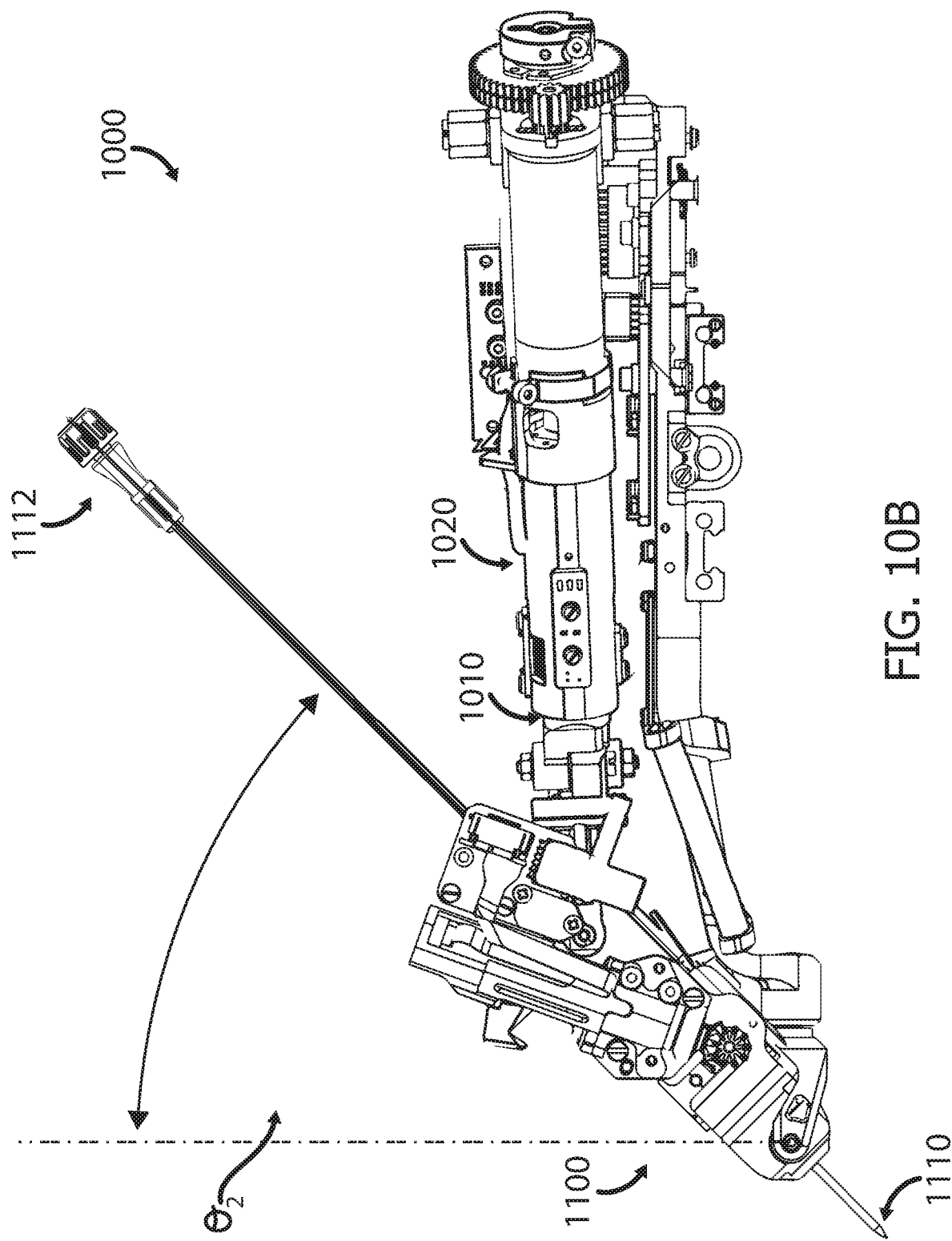

FIG. 10B shows a side view of the top assembly 1000 with the insertion assembly 1100 at its maximal forward-directed rotation angle $\theta_2=45°$, i.e., the insertion assembly 1100 is maximally rotated about the X axis toward the device. A forward angle is achieved by propelling both pistons 1010 backward, into the cylinders 1020, causing the needle head 1112 to rotate backward and the needle tip 1110 to point forward, i.e., away from the device.

Figure 10C:
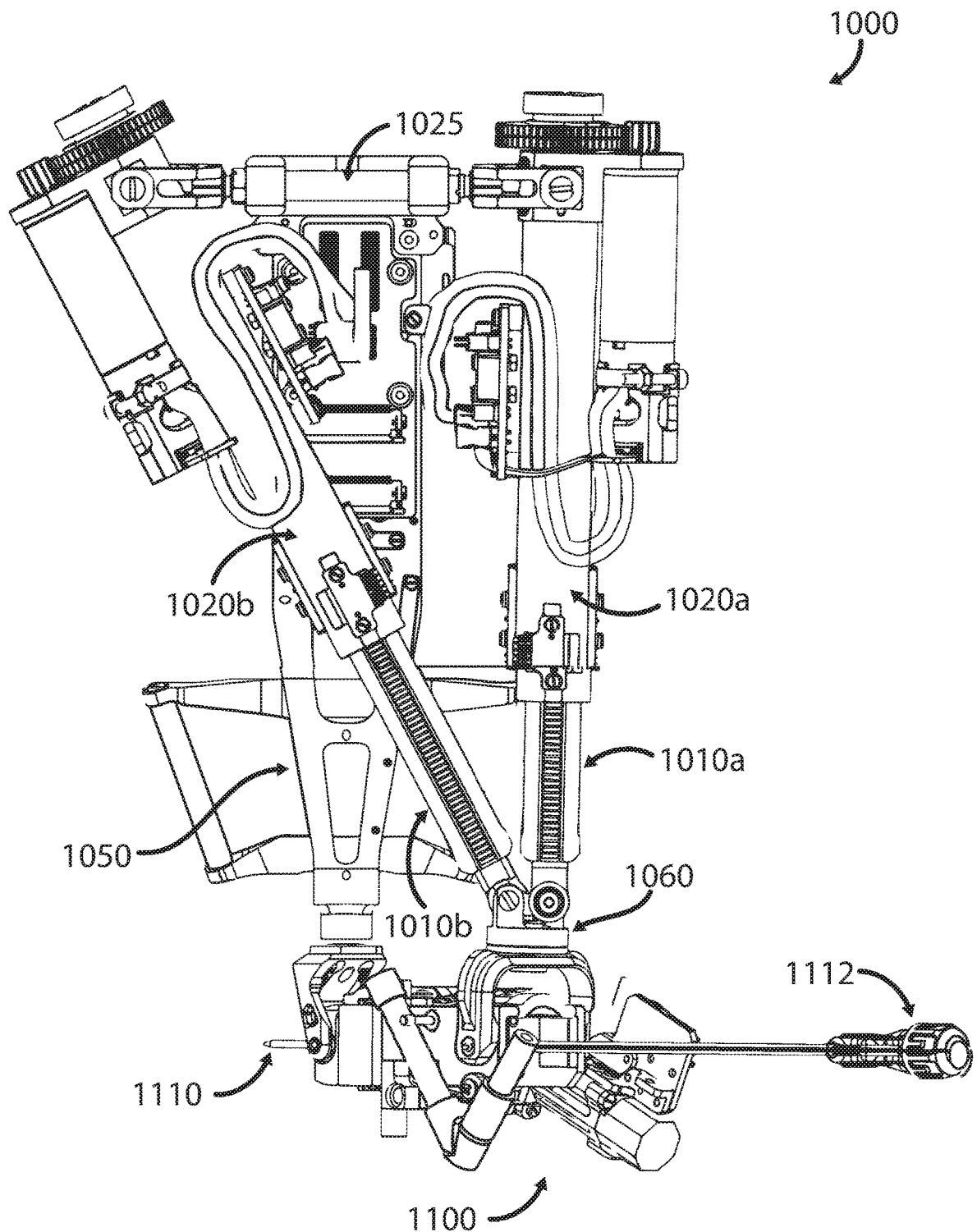

FIG. 10C shows a top view of the top assembly 1000 with the insertion assembly 1100 at its maximal right rotation angle $\theta_3=45°$ (shown below in FIG. 10E), i.e., the insertion assembly 1100 is maximally rotated to the right about the Z axis (the direction "right" referring to the page layout). A right angle is achieved by rotating both cylinders 1020a and 1020b to the right. Such rotation is achieved by propelling the left piston 1010b further out of the left cylinder 1020b than the right piston 1010a is propelled out of the right cylinder 1020b. Rotation of the insertion assembly 1100 to the right causes the needle head 1112 to rotate to the right, such that the needle tip 1110 points to the left.

Figure 10D:
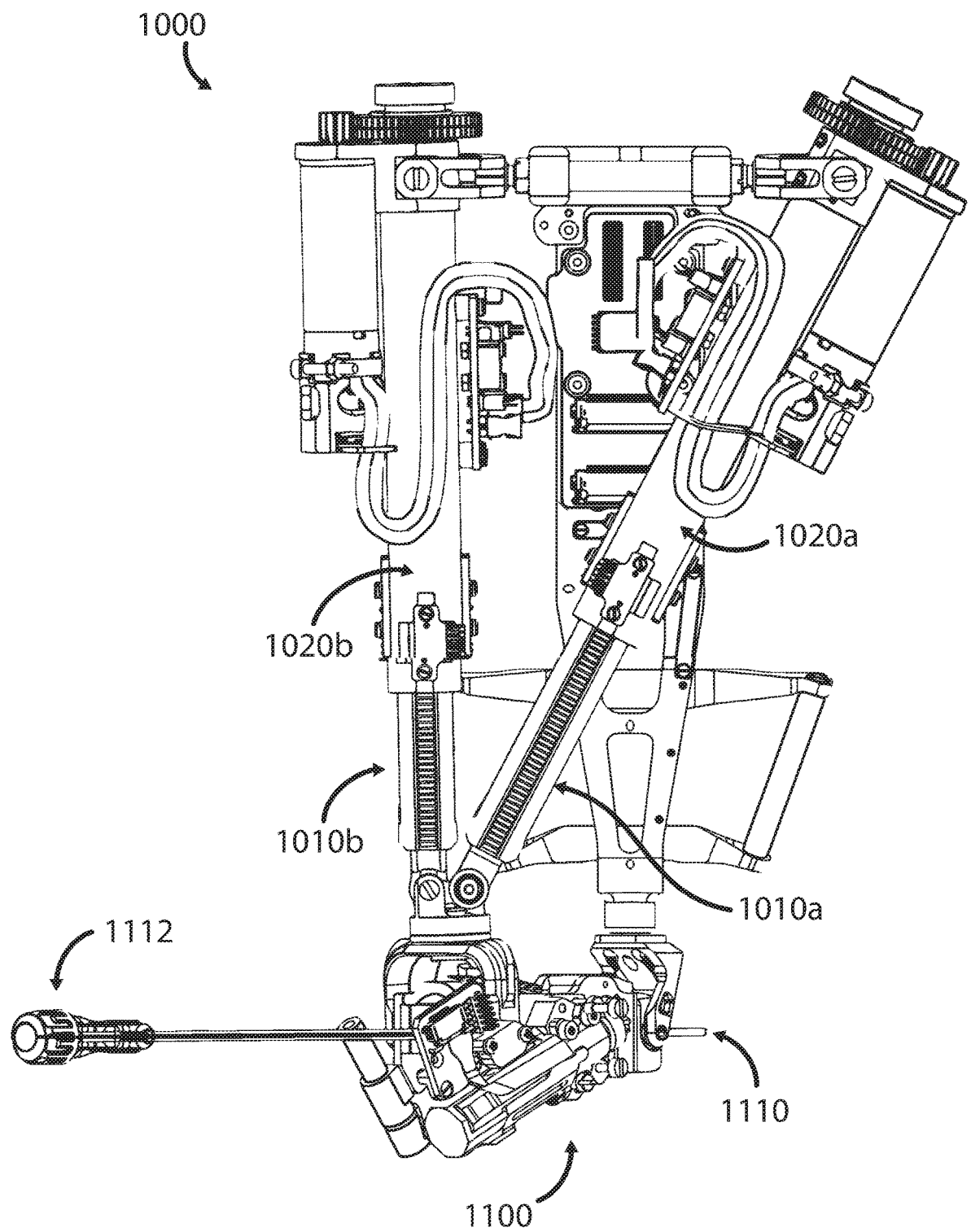

FIG. 10D shows a top view of the top assembly 1000 with the insertion assembly 1100 at its maximal left rotation angle $\theta_4=45°$ (shown below in FIG. 10E), i.e., the insertion assembly 1100 is maximally rotated to the left about the Z axis. A left angle is achieved by rotating both cylinders 1020a, 1020b to the left. Such rotation is achieved by propelling the right piston 1010a further out of the right cylinder 1020a than the left piston 1010b is propelled out of the left cylinder 1020b. Rotation of the insertion assembly 1100 to the left causes the needle head 1112 to rotate to the left, such that the needle tip 1110 points to the right.

As shown in FIGS. 10A-10D, as the insertion assembly 1100 is being rotated throughout its entire rotation range, the top assembly's arm member 1050 remains stationary and the cylinders 1020a and 1020b, the pistons 1010a and 1010b, the shaft 1025 and the common joint 1060 all remain on the same plane.

Figure 10E:
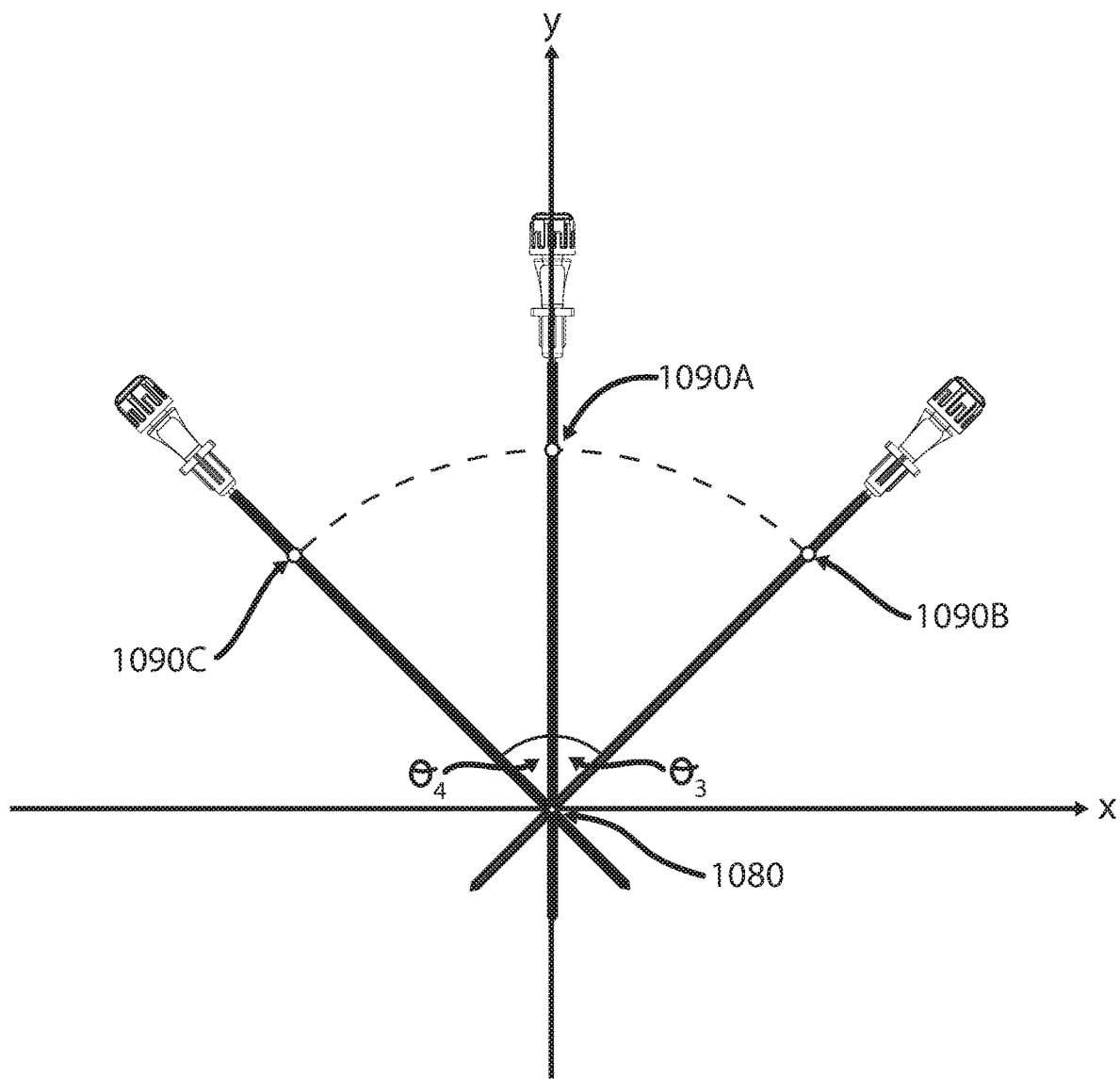

FIG. 10E demonstrates the maximal right and left rotation angles, $\theta_3$ and $\theta_4$ respectively, of the insertion assembly of FIGS. 10C and 10D. Also shown are the locations 1090A, 1090B and 1090C of the top gimbal when the needle is parallel to the Y axis and when the insertion assembly reaches its maximal right and left rotation angles, respectively. The top gimbal's trajectory between the maximal right and left rotation angles forms an arc on the X-Y plane. It can be appreciated that the top gimbal's trajectory as the insertion assembly is being rotated between the maximal forward angle and the maximal backward angle also forms an arc, on the Z-Y plane.

It is to be understood, that although in FIGS. 10A-10E the maximal needle rotation angles are $\theta_1=\theta_2=\theta_3=\theta_4=45°$, this is done for simplicity reasons alone. The maximal rotation angles $\theta_1$, $\theta_2$, $\theta_3$ and $\theta_4$ are not necessarily equal to each other. Further, they are not limited to 45°, and each may be higher or lower than 45°.

Figure 11:
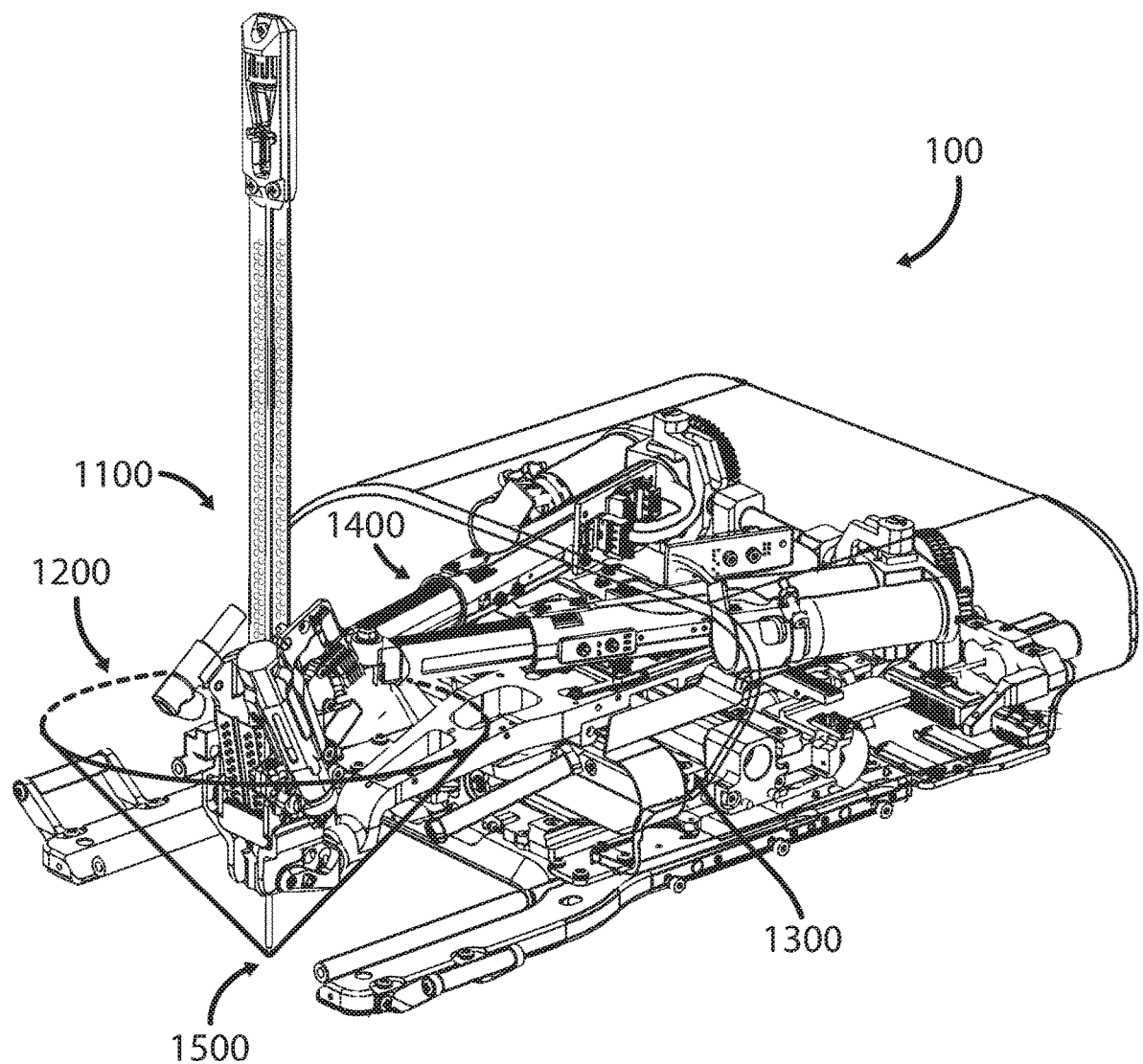
FIG. 11 depicts an overall angular workspace of an exemplary insertion assembly.

FIG. 11 depicts the overall workspace 1200 of the longitudinal axis of the insertion assembly 1100 having two rotational degrees of freedom, the first depicted in FIGS. 10A-10B and the second depicted in FIGS. 10C-10E. In some implementations, the Remote Center of Motion (RCM) of the insertion assembly 1100 may be virtual and located at the needle's entry point. Although the rotation axis of the insertion assembly is located at the bottom gimbal of the device's top assembly, as shown in FIG. 10E, the location of the virtual RCM is maintained at the needle's entry point via linear movements of the X platform along the Z axis and/or of the top assembly along the X axis.

Once the needle entry point is selected, the user may set the selected entry point as the virtual RCM. The system's software can then determine, using a reverse kinematics algorithm, as described, for example, in abovementioned U.S. Pat. No. 8,348,861, the linear movements required from the X platform and/or the top assembly, while the insertion assembly is being rotated, in order to maintain the entry point as the virtual RCM. The virtual RCM being maintained at the needle entry point prevents skin/tissue tearing in case a linear needle trajectory is not possible to follow and/or if the planned trajectory (linear or otherwise) requires adjustments as the needle is being inserted.

The workspace 1200 may form a cone shape, with its vertex 1500, being the virtual RCM, located at the needle's entry point. It can be appreciated that the insertion assembly's workspace is not necessarily symmetrical in all axis. If the maximal rotation angles are identical about all axis, e.g., as shown above in FIGS. 10A-10E, then the workspace is symmetrical about all axis, as shown in FIG. 11, i.e., the transverse cross-section of the formed cone is a circle. However, if the maximal rotation angles about the X axis are different from the maximal rotation angles about the Z axis, e.g., $\theta_1=\theta_2=45°$ and $\theta_3=\theta_4=55°$, the transverse cross-section of the formed cone is an ellipse. In some implementations, the maximal rotation angles may differ in each direction. Further, the angular workspace is not necessarily equal to the rotation about X axis and to the rotation about the Z axis, such that the workspace may be, for example, rectangular.

Although particular implementations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the disclosure as defined by the claims. Other aspects, advantages, and modifications are considered to be within the scope of the following claims. The claims presented are representative of the implementations and features disclosed herein. Other unclaimed implementations and features are also contemplated. Accordingly, other implementations are within the scope of the following claims.

The invention claimed is:

1. An automated device for inserting a medical tool into a body of a subject, comprising:
a device base;
a first platform coupled to said device base and comprising a first portion of a first driving mechanism;
a second platform coupled to said first platform and comprising:
a second portion of said first driving mechanism, said first driving mechanism comprising at least a first motor and being configured to propel said second platform in a first linear direction; and
a first portion of a second driving mechanism;
a third platform coupled to said second platform and comprising:
a second portion of said second driving mechanism, said second driving mechanism comprising at least a second motor and being configured to propel said third platform in a second linear direction substantially perpendicular to the first linear direction; and
first and second pistons connected to a common joint at their distal ends; and
an end effector coupled to said common joint and configured for coupling said medical tool thereto.

2. The automated device according to claim 1, wherein axes of said first and second pistons and a line connecting said piston axes through said common joint, are located substantially in a single plane.

3. The automated device according to claim 2, further comprising:
first and second cylinders, wherein at least a portion of said first piston is positioned within the first cylinder, and at least a portion of said second piston is positioned within the second cylinder;
a fourth driving mechanism configured to controllably propel said first piston in and out of the first cylinder; and
a fifth driving mechanism configured to controllably propel said second piston in and out of the second cylinder.

4. The automated device according to claim 3, wherein proximal ends of said first and second cylinders are coupled to a single shaft, and wherein axes of said first and second cylinders and of said single shaft are located in said single plane.

5. The automated device according to claim 4, wherein said proximal ends of said first and second cylinders are coupled to said single shaft via cylinder end joints, each cylinder end joint having at least one rotational degree of freedom.

6. The automated device according to claim 3, wherein each of said fourth and fifth driving mechanisms comprises:
a threaded shaft;
an internally threaded nut operatively coupled to said threaded shaft and rigidly connected to a piston of said first and second pistons,
wherein rotation of said threaded shaft results in linear movement of said piston of said first and second pistons.

7. The automated device according to claim 1, further comprising an insertion module configured for receiving said medical tool and for coupling to said end effector, to couple said medical tool to said end effector.

8. The automated device according to claim 7, wherein said end effector comprises a first portion of a third driving mechanism and said insertion module comprises a second portion of said third driving mechanism, operatively coupleable to said first portion of said third driving mechanism, wherein said third driving mechanism comprises at least a third motor and is configured to impart movement to said medical tool in the direction of the body of the subject.

9. The automated device according to claim 8, wherein said first portion of said third driving mechanism comprises said third motor, and said second portion of said third driving mechanism comprises two rollers, and wherein upon said medical tool being received by said insertion module, said medical tool is disposed between said two rollers, such that counter-rotation of said two rollers by said third motor results in linear movement of said medical tool between said two rollers.

10. The automated device according to claim 1, wherein said distal ends of said first and second pistons are coupled to said common joint via piston end joints, each piston end joint having at least one rotational degree of freedom.

11. The automated device according to claim 1, further comprising a first gimbal, and wherein said end effector is coupled to said common joint via said first gimbal.

12. The automated device according to claim 1, wherein said second platform further comprises an extending arm and a second gimbal configured for coupling said end effector to said extending arm.

13. The automated device according to claim 1, wherein said first portion of said first driving mechanism comprises said first motor and a first threaded shaft, and said second portion of said first driving mechanism comprises a first internally threaded nut configured to receive therein said first threaded shaft, such that rotation of said first threaded shaft by said first motor results in linear movement of said second platform.

14. The automated device according to claim 1, wherein said first portion of said second driving mechanism comprises said second motor and a second threaded shaft, and said second portion of said second driving mechanism comprises a second internally threaded nut configured to receive therein said second threaded shaft, such that rotation of said second threaded shaft by said second motor results in linear movement of said third platform.

15. The automated device according to claim 1, further comprising one or more sensors coupled to one or more of said first platform, said second platform, said third platform, said first piston, said second piston and said end effector.

16. The automated device according to claim 15, wherein at least a first sensor of said one or more sensors is configured to measure a parameter associated with an interaction between said medical tool and a bodily tissue.

17. The automated device according to claim 15, wherein at least a second sensor of said one or more sensors is configured to monitor movement of one or more of said first platform, said second platform, said third platform, said first piston and said second piston.

18. The automated device according to claim 1, further comprising at least one registration element.

19. The automated device according to claim 1, wherein the device base is configured for securing to the body of the subject.

20. The automated device according to claim 1, further comprising a mounting base configured for securing to the body of the subject and for coupling said device base thereto.

* * * * *